(12) United States Patent
Elias et al.

(10) Patent No.: US 7,214,373 B2
(45) Date of Patent: May 8, 2007

(54) METHODS, COMPOSITIONS AND KITS RELATING TO CHITINASES AND CHITINASE-LIKE MOLECULES AND INFLAMMATORY DISEASE

(75) Inventors: Jack A. Elias, Woodbridge, CT (US); Zhou Zhu, Woodbridge, CT (US)

(73) Assignee: Yale University, New Haven, CT (US)

( * ) Notice: Subject to any disclaimer, the term of this patent is extended or adjusted under 35 U.S.C. 154(b) by 470 days.

(21) Appl. No.: 10/202,436

(22) Filed: Jul. 23, 2002

(65) Prior Publication Data
US 2003/0049261 A1 Mar. 13, 2003

Related U.S. Application Data

(60) Provisional application No. 60/307,432, filed on Jul. 24, 2001.

(51) Int. Cl.
*A61K 39/395* (2006.01)
(52) U.S. Cl. .............................. 424/139.1; 424/141.1; 424/146.1; 530/387.9; 530/388.26
(58) Field of Classification Search ............ 424/133.1, 424/135.1, 141.1, 146.1; 530/387.3, 388.1, 530/388
See application file for complete search history.

(56) References Cited

U.S. PATENT DOCUMENTS

| | | | |
|---|---|---|---|
| 5,070,191 A | 12/1991 | Yamada | |
| 5,413,991 A | 5/1995 | Yamada | |
| 6,844,179 B1 * | 1/2005 | Nakanishi et al. | 435/201 |
| 2003/0087414 A1 * | 5/2003 | Aerts et al. | 435/226 |
| 2005/0163767 A1 * | 7/2005 | Nakanishi et al. | 424/130.1 |

FOREIGN PATENT DOCUMENTS

| | | |
|---|---|---|
| EP | 1 231 270 A1 | 9/2000 |
| WO | WO 0136633 A1 * | 5/2001 |
| WO | WO 02/23991 | 3/2002 |

OTHER PUBLICATIONS

Clark, M. "Antibody humanization: a case of the 'Emperor's new clothes'?" (2000) immunology Today, 21:397-402.*
The Merck Manual of Diagnosis and Therapy, 17th ed, 1999, eds. Beers and Berkow, Merck Research Laboratoroies, pp. 601-616.*
Genbank sequence AF290003, Feb. 27, 2001, pp. 1-2.*
Genbank sequence AF290004, Feb. 27, 2001, pp. 1-2.*
Campbell, A. M., Monoclonal Antibody Technology, 1984, Elsevier Science Publishing Company Inc., pp. 1-32.*
The Merck Manual, 17th edition, 1999, editors Beers and Berkow, Merck Research Laboratories, pp. 568-583.*
Bleau et al., 1999, EXS 87:211-221.
Boot et al., 1998, J. Biol. Chem. 273:25680-25685.
Boot et al., 2001, J. Biol. Chem. 276:6770-6778.
Bradding et al., 1994, Am. J. Respir. Cell Mol. Biol. 10:471-480.
Chang et al., 2001, J. Biol. Chem. 276:17497-17506.
Elias et al., 1999, J. Clin. Invest. 104:1001-1006.
Funke et al., 1989, Comp. Biochem Physiol. 94B:691-695.
Gossen et al., 1995, Science 268:1766-1769.
Grünig et al. 1998, Science 282:2261-2263.
Guo et al., 2000, J. Biol. Chem. 275:8032-8037.
Guoping et al., 1997, J. Cell. Biochem. 67:257-264.
Hamelmann et al. 1997, Am. J. Resp. Crit. Care Med. 156:766-775.
Hamid et al., 1991, J. Clin. Invest. 87:1541-1546.
Heinzmann et al., 2000, Hum. Mol. Genet. 9:549-559.
Izumida et al., 1995, J. Mar. Biotechnol. 2:163-166.
Izumida et al., 1996, J. Antibiotics 49:76-80.
Jin et al., 1998, Genetics 54:316-322.
Kato et al., 1995, Tetrahedron. Lett. 36:2133-2136.
Kotsimbos et al., 1996, Proc. Assoc. Am. Physicians 108:368-373.
Nicolaides et al., 1997, Proc. Natl. Acad. Sci. USA 94:13175-13180.
Nishimoto et al., 1991, J. Antibiotics 44:716-72.
Owhashi et al., 2000, J. Biol. Chem. 275:1279-1286.
Ray et al. 1997, J. Clin. Invest. 100:2501-2511.
Ray et al., 1999, J. Clin. Invest. 104:985-993.
Seferian et al., 2000, Vaccine 19:661-668.
Shibata et al., 2000 J. Immunol. 164:1314-1321.
Snol et al, 2000, J. Clin. Invest. 105:1027-1030.
Ward et al., 2001, Am. J. Pathol. 158:323-332.
Webb et al., 2001, J. Biol. Chem. 276:41969-41976.
Wills-Karp, 1998, Science 282:2258-2260.
Xu et al., 1997, Lancet 350:1431-1434.
Yang et al. 1998, J. Exp. Med. 188:1739-1750.
Zhou et al, 1993, J. Antibiotics 46:1582-1588.
Zhu et al. 1999, J. Clin. Invest. 103:779-788.
Vestbo et al., "Update on the 'Dutch hypothesis' for chronic respiratory disease", Thorax, 53(Suppl. 2): S15-S19 (1998).
Fülöp and Falus, "Possibilities and results in the wide-scale genomic analysis of inflammation," Inflammation Research, 53:517-522 (2004).
Lindsay, Mark "Target discovery," Nature Reviews, 2:831-838(2003).

* cited by examiner

*Primary Examiner*—G. R. Ewoldt
*Assistant Examiner*—Michael Szperka
(74) *Attorney, Agent, or Firm*—Fish & Neave IP Group Ropes & Gray LLP

(57) ABSTRACT

The present invention includes compositions and methods for the treatment of inflammatory disease (e.g., asthma, COPD, inflammatory bowel disease, atopic dermatitis, atopy, allergy, allergic rhinitis, scleroderma, and the like), relating to inhibiting a chitinase-like molecule. The invention further includes methods to identify new compounds for the treatment of inflammatory disease, including, but not limited to, asthma, COPD and the like. This is because the present invention demonstrates, for the first time, that expression of IL-13, and of a chitinase-like molecule, mediates and/or is associated with inflammatory disease and that inhibiting the chitinase-like molecule treats and even prevents, the disease. Thus, the invention relates to the novel discovery that inhibiting a chitinase-like molecule treats and prevents an inflammatory disease.

5 Claims, 23 Drawing Sheets

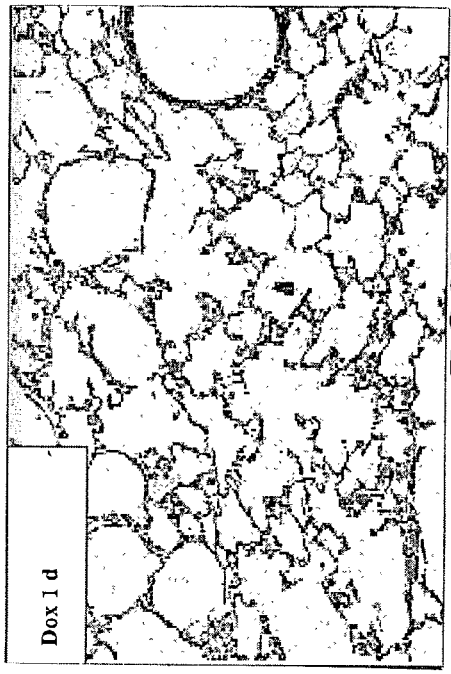
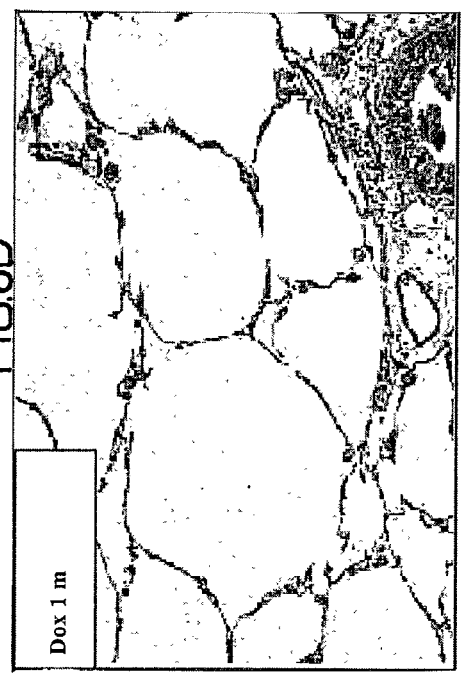
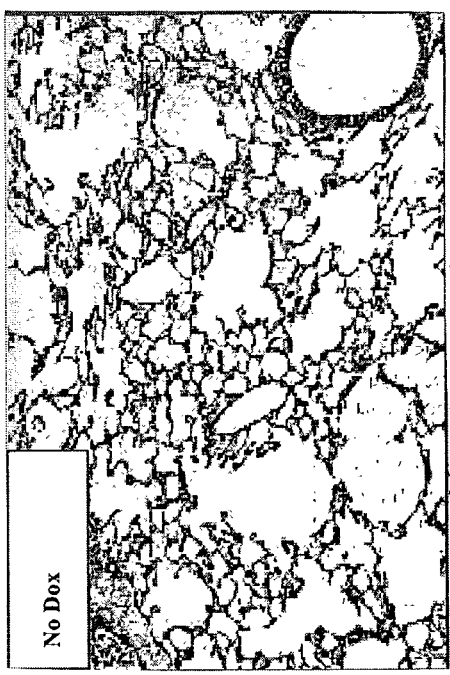
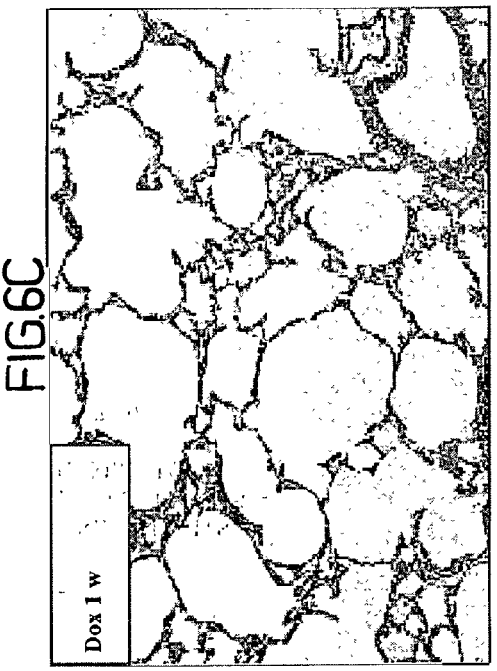

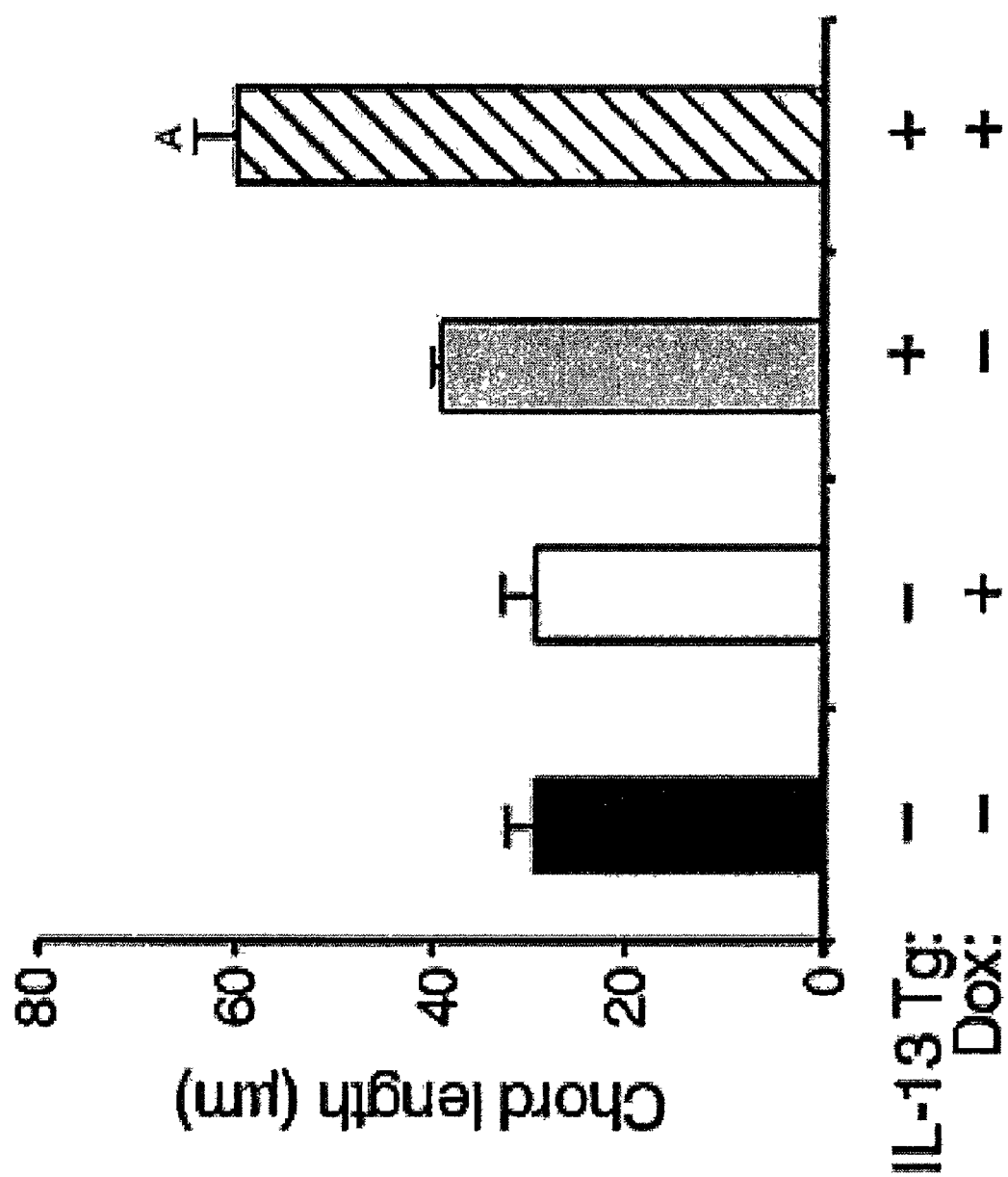

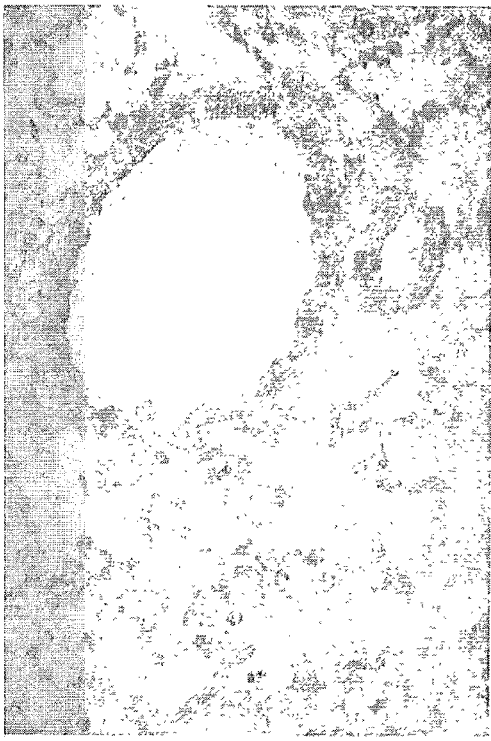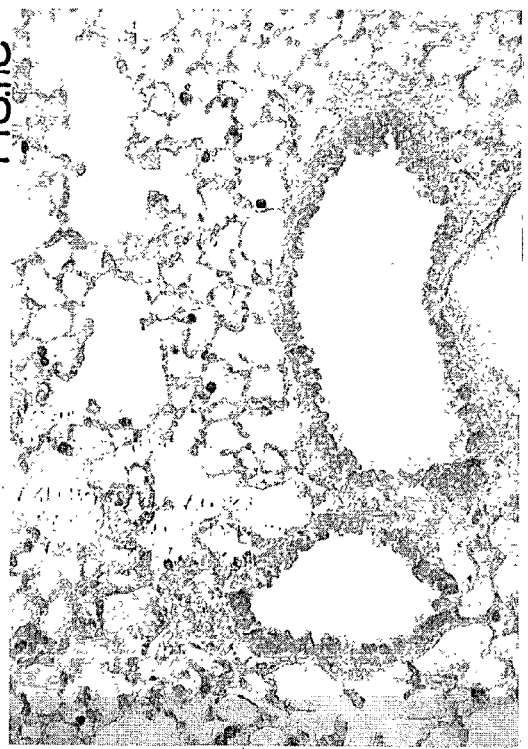

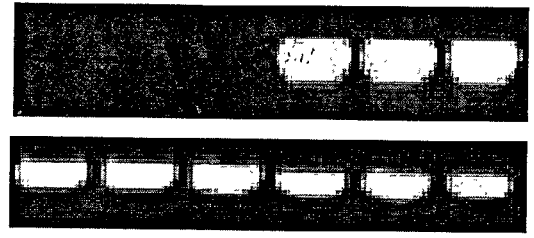
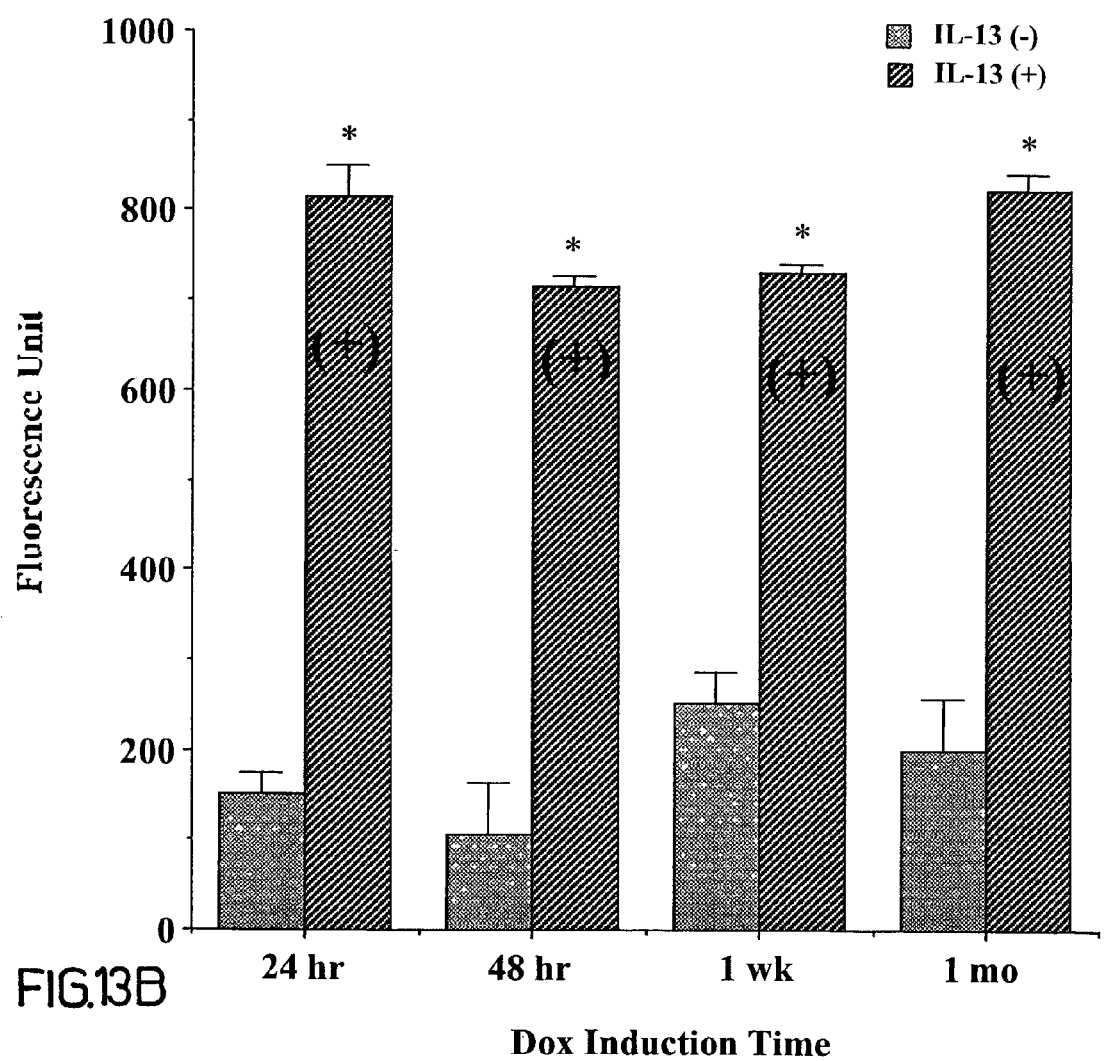
FIG.13A
FIG.13B

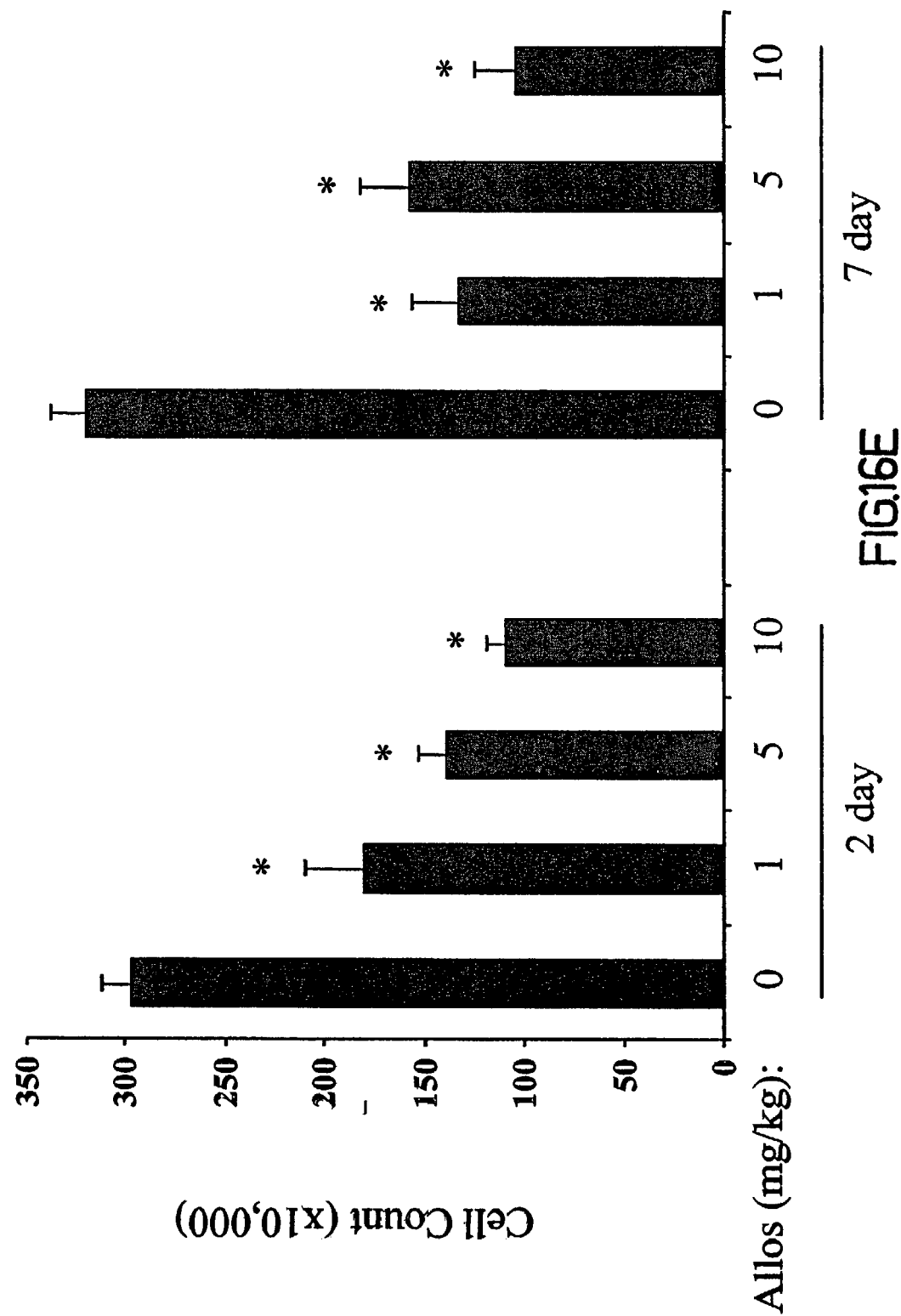

SEQUENCE LISTING

<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: YM-1 Forward Primer

<400> SEQUENCE: 1
tggaattggt gcccctacaa                                               20

<210> SEQ ID NO 2
<211> LENGTH: 20
<212> TYPE: DNA
<213> ORGANISM: Artificial
<220> FEATURE:
<223> OTHER INFORMATION: YM-1 Reverse Primer

<400> SEQUENCE: 2
aacttgcact gtgtatattg                                               20

<210> SEQ ID NO 3
<211> LENGTH: 18
<212> TYPE: DNA
<213> ORGANISM: Artificial
<220> FEATURE:
<223> OTHER INFORMATION: YM-2 Forward Primer

<400> SEQUENCE: 3
aacctcagac attcatta                                                 18

<210> SEQ ID NO 4
<211> LENGTH: 21
<212> TYPE: DNA
<213> ORGANISM: Artificial
<220> FEATURE:
<223> OTHER INFORMATION: YM-2 Reverse Primer

<400> SEQUENCE: 4
tggtccttcc agtaggtaat a                                             21

<210> SEQ ID NO 5
<211> LENGTH: 20
<212> TYPE: DNA
<213> ORGANISM: Artificial
<220> FEATURE:
<223> OTHER INFORMATION: YM-3 Forward Primer

<400> SEQUENCE: 5
tataaatctc catttgacac                                               20

<210> SEQ ID NO 6
<211> LENGTH: 20
<212> TYPE: DNA
<213> ORGANISM: Artificial
<220> FEATURE:
<223> OTHER INFORMATION: YM-3 Reverse Primer

<400> SEQUENCE: 6
cctaatttat tgtccttgac                                               20

<210> SEQ ID NO 7
<211> LENGTH: 28

```
<212> TYPE: DNA
<213> ORGANISM: Artificial
<220> FEATURE:
<223> OTHER INFORMATION: AMCase Forward Primer

<400> SEQUENCE: 7
atctgcagtg gacacacctt catcctga                                28

<210> SEQ ID NO 8
<211> LENGTH: 28
<212> TYPE: DNA
<213> ORGANISM: Artificial
<220> FEATURE:
<223> OTHER INFORMATION: AMCase Reverse Primer

<400> SEQUENCE: 8
atgaattcaa caagccctgc ttgacaat                                28

<210> SEQ ID NO 9
<211> LENGTH: 22
<212> TYPE: DNA
<213> ORGANISM: Artificial
<220> FEATURE:
<223> OTHER INFORMATION: YM Antisense In Situ Hybridization Probe

<400> SEQUENCE: 9
tcctcgagac ccagggtact gc                                      22

<210> SEQ ID NO 10
<211> LENGTH: 24
<212> TYPE: DNA
<213> ORGANISM: Artificial
<220> FEATURE:
<223> OTHER INFORMATION: YM Sense In Situ Hybridization Probe

<400> SEQUENCE: 10
tatctagagg atcttcctac cagc                                    24

<210> SEQ ID NO 11
<211> LENGTH: 29
<212> TYPE: DNA
<213> ORGANISM: Artificial
<220> FEATURE:
<223> OTHER INFORMATION: AMCase Antisense In Situ Hybridization Probe

<400> SEQUENCE: 11
tcgctcgaga acaagccctg cttgacaat                               29

<210> SEQ ID NO 12
<211> LENGTH: 28
<212> TYPE: DNA
<213> ORGANISM: Artificial
<220> FEATURE:
<223> OTHER INFORMATION: AMCase sense In Situ Hybridization Probe

<400> SEQUENCE: 12
gctctagatg gacacacctt catcctga                                28

<210> SEQ ID NO 13
<211> LENGTH: 19
<212> TYPE: PRT
<213> ORGANISM: Artificial
<220> FEATURE:
<223> OTHER INFORMATION: Anti-AMCase Antibody Immunizing Peptide

<400> SEQUENCE: 13
```

Ala Asp Lys Ala Asp Gly Leu Tyr Pro Val Ala Asp Asp Arg Asn Ala
1               5                   10                  15
Phe Trp Gln

<210> SEQ ID NO 14
<211> LENGTH: 1038
<212> TYPE: DNA
<213> ORGANISM: Artificial
<220> FEATURE:
<223> OTHER INFORMATION: AMCase sense in situ hybridization probe

<400> SEQUENCE: 14

```
tggagagaac agcccctct acaaataccc gactgacacc ggcagcaacg cctacctcaa      60
tgtggattat gtcatgaact actggaagga caatggagca ccagctgaga agctcatcgt    120
tggattccct acctatggac acaacttcat cctgagcaac ccctccaaca ctggaattgg    180
tgcccccacc tctggtgctg gtcctgctgg gccctatgcc aaggagtctg ggatctgggc    240
ttactacgag atctgtacct tcctgaaaaa tggagccact cagggatggg atgcccctca    300
ggaagtgcct tatgcctatc agggcaatgt gtgggttggc tatgacaacg tcaagagctt    360
cgatattaag gctcaatggc ttaagcacaa caaatctgga ggcgccatgg tctgggccat    420
tgatctggat gacttcactg gcactttctg caaccaggg aagtttcccc taatctccac    480
cctgaagaag gccctcgggc tgcagagtgc aagttgcacg gctccagctc agcccattga    540
gccaataact gctgctccca gtggcagcgg gaacggagc gggagtagca gctctggagg    600
cagctcggga ggcagtggat tcttgtgctt ggcagagcaa acgagctcta accccgtggg    660
caaattacca gaagatgcct tctgggcact gcgtgaatgg agtcacgtac caggcagaac    720
ttgccaggcc gggcttgtcc ttcgagacca gctgtgaatg ctgcaactgg cattaacct    780
gacctggtct atattcccta gagttccagt ctctttggct taggacatgg ttggcccta    840
aacttaaagg ctcctggcaa gtagaaattc aggcagctca aaaccagaac cgcaggagga    900
caggaaagga gaagaacaaa cagcgggggc ggcgcgcaat aaagacacac ccagagggcg    960
caacacggag aggaccccga gatagtcgaa ccagaggggc ccaaaaagag agagcggaat   1020
aaaagagaga cggagcgg                                                 1038
```

METHODS, COMPOSITIONS AND KITS RELATING TO CHITINASES AND CHITINASE-LIKE MOLECULES AND INFLAMMATORY DISEASE

CROSS-REFERENCE TO RELATED APPLICATIONS

This application is entitled to priority pursuant to 35 U.S.C. §119(e) to U.S. Provisional Patent Application No. 60/307,432, which was filed on Jul. 24, 2001.

STATEMENT REGARDING FEDERALLY SPONSORED RESEARCH OR DEVELOPMENT

This invention was supported in part by funds obtained from the U.S. Government (National Institutes of Health Grant Numbers R01-HL-64242, R01-HL66571, and P01-HL-56389) and the U.S. Government may therefore have certain rights in the invention.

BACKGROUND OF THE INVENTION

The prevalence of asthma has been steadily increasing for the past two decades, with an estimated 17 million cases in the United States alone. Once believed to be primarily a dysfunction in the contractile mechanisms of airway smooth muscles, recent studies have indicated the role of the immune system and inflammation in asthma and other pulmonary diseases.

Asthma is now characterized as a complex inflammatory disease attributed to the inappropriate stimulation of the immune system. In some cases, the inflammation is triggered by airborne antigens. In others, exogenous triggers cannot be defined (intrinsic asthma). The immune cells and mediators implicated in asthmatic inflammation include IgE, mast cells, eosinophils, T cells, interleukin-4 (IL-4), IL-5, IL-9, IL-13 and other cytokines (Bradding et al., 1994, Am. J. Respir. Cell Mol. Biol. 10:471–480; Bradding et al., 1997, Airway Wall Remodeling in Asthma, CRC Press, Boca Raton, Fla.; Nicolaides et al., 1997, Proc. Natl. Acad. Sci. USA 94:13175–13180; Wills-Karp, 1998, Science 282:2258–2260; Hamid et al., 1991, J. Clin. Invest. 87:1541–1546; Kotsimbos et al., 1996, Proc. Assoc. Am. Physicians 108:368–373). Of these immune cells and mediators, the role of T-helper type 2 (Th2) cells and cytokines is proving to be increasingly important, as they are believed to be responsible for initiation and maintenance of airway inflammation, as well as vital to B cell regulation, eosinophil function, mucus responses, and stimulation of airway remodeling (Elias et al., 1999, J. Clin. Invest. 104:1001–1006; Ray et al., 1999, J. Clin. Invest. 104: 985–993).

Immune-mediated inflammation is thought to lead to airway remodeling, or structural modifications, in the asthmatic airway. The end result of remodeling is believed to contribute to both the symptoms and physiological dysregulation of asthma. Remodeling is often characterized by airway thickening, mucus metaplasia, epithelial hypertrophy and airway fibrosis. Extensive fibrosis is widely considered to increase disease severity, airway hyperresponsiveness (AHR) and contribute to the generation of incompletely reversible airway obstruction (Elias et al., 1999, J. Clin. Invest. 104:1001–1006). Therefore, the successful design of therapeutics for the treatment of asthma requires an understanding of both the mechanisms of inflammation and the processes of injury and wound healing in the respiratory system.

Two prominent cytokines, IL-4 and IL-13, are believed to play an important role in the inflammation and airway remodeling of asthma and other pulmonary diseases. IL-4 and IL-13 are similar in that they are both produced by the same subset of Th2 helper T cells, have overlapping effector profiles, and share a receptor component and signaling pathways. However, the critical role of IL-13 over IL-4 in AHR, eosinophil recruitment, mucus overproduction, and other symptoms of asthma has been conclusively demonstrated (Wills-Karp, 1998, Science 282:2258–2260, Grunig et al. 1998, Science 282:2261–2263). Overexpression of IL-13 in the murine lung results in eosinophil, lymphocyte, and macrophage rich inflammation, mucus metaplasia, airway fibrosis, and AHR after methacholine challenge (Zheng et al., 1999 J. Clin. Invest. 103:779–788). Further, polymorphisms in both the IL-13 promoter and the coding region have been associated with the asthmatic phenotype (Heinzmann et al., 2000, Hum. Mol. Genet. 9:549–559). These results suggest that abnormal IL-13 production is a critical component of asthmatic inflammation and airway remodeling.

The role of IL-13 in inflammatory pulmonary diseases is not limited to asthma. Chronic obstructive pulmonary disease (COPD, clinically defined as chronic bronchitis, emphysema, and chronic obstructive lung disease) has long been thought of as a distinct disease from asthma. However, the similarities between the two diseases have been noted and have resulted in the formulation of the "Dutch Hypothesis", that was first proposed in 1961. The most recent revision of the Dutch Hypothesis proposes that asthma and COPD, in some individuals, are not distinct processes, and that common pathogenic mechanism underlie these disorders. The hypothesis further states that a genetic predisposition to develop atopy, asthma, AHR and/or increased levels of IgE predispose cigarette smokers to develop COPD (Vestbo and Prescott, 1998, Thorax 53(Suppl. 2): S15–S19). Further, overexpression of IL-13 in the murine lung causes emphysema and COPD-like mucus metaplasia, IL-13 is overexpressed in biopsy and autopsy lung tissue from patients with COPD, and polymorphisms of IL-13 have been described that correlate with the presence of COPD. When these results are viewed in light of the Dutch Hypothesis, not only are asthma and COPD more closely related than previously thought, but the central role of IL-13 dysregulation in these pulmonary inflammatory disorders becomes more prominent.

The progress in illuminating the underlying mechanisms and causes of asthma, COPD and related pulmonary inflammatory disorders is striking considering the fact that what was once thought of as a malfunction of bronchial muscle contraction can now be linked to specific cytokines and cell types. Despite this progress, asthma remains, along with tuberculosis and AIDS, the only chronic disease with an increasing death rate. In addition, by 2020, COPD is expected to be the fourth leading cause of death in the world.

To counter the increasing morbidity and mortality due to asthma, the arsenal of medications for the treatment of asthma is ever increasing.

Asthma medications fall into two general categories, controllers and relievers. Controllers are for the prevention of asthma attacks before symptoms arise, and relievers are taken during the midst of an asthma attack. Controllers include corticosteroids, widely considered the most potent and effective anti-inflammatory drugs available, cromolyn sodium and nedocromil, milder anti-inflammatories often used in children, and long-acting beta-2 agonists, which are bronchodilators. Relievers include short acting beta-2 agonists and anticholinergenics, which are often used a supplements or alternatives to beta-2 agonists.

While corticosteroids and other therapeutics target the inflammatory-mediated symptoms of asthma, they often have broad-ranging immunosuppressive properties, as well as other deleterious side effects. As the physiological and biological mechanisms of asthma are elucidated, development of specific and effective drugs should closely follow, and the symptoms, morbidity, and mortality of asthma should drop, instead of its current rise. However, despite increased understanding of the underlying disease mechanism and despite the increasing incidence of asthma, and morbidity and death therefrom, there are currently a limited number of effective and safe treatments for asthma, COPD and other inflammatory diseases. In addition, there are no pharmacologic drugs that alter the progression of COPD.

Thus, there is a long felt and acute need for specific, effective treatments for asthma, COPD, and other inflammatory diseases. The present invention meets this need.

BRIEF SUMMARY OF THE INVENTION

A method of treating an inflammatory disease in a mammal wherein the disease is associated with an increased level of a chitinase-like molecule. The method comprises administering an effective amount of a chitinase-like molecule inhibitor to the mammal, thereby treating the inflammatory disease in the mammal.

In one aspect, the mammal is a human.

In another aspect, the chitinase-like molecule is selected from the group consisting of a YM-1, a YM-2, an acidic mammalian chitinase (AMCase), an oviductal glycoprotein 1, a cartilage glycoprotein 1, a chitotriosidase, a mucin 9, a cartilage glycoprotein-39, and a chondrocyte protein 39.

In another aspect, the chitinase-like molecule inhibitor is selected from the group consisting of a chemical compound, an antibody, a ribozyme, a nucleic acid, and an antisense nucleic acid molecule.

In yet another aspect, the chemical compound is selected from the group consisting of allosamidin, glucoallosamidin A, glucoallosamidin B, methyl-N-demethylallosamidin, demethylallosamidin, didemthylallosamidin, stylogaunidine, a styloguanidine derivative, dipeptide cyclo-(L-Arg-D-Pro), dipeptide cyclo-(L-Arg-L-Pro), dipeptide cyclo-(D-Arg-D-Pro), dipeptide cyclo-(D-Arg-L-Pro), riboflavin, a flavin derivative, copper, zinc, and mercury.

In a further aspect, the antibody specifically binds with a chitinase-like molecule selected from the group consisting of a YM-1, a YM-2, an acidic mammalian chitinase (AMCase), an oviductal glycoprotein 1, a cartilage glycoprotein 1, a chitotriosidase, a mucin 9, a cartilage glycoprotein-39, and a chondrocyte protein 39.

In another aspect, the antisense nucleic acid molecule is an isolated nucleic acid complementary to an isolated nucleic acid encoding the chitinase-like molecule, or a fragment thereof.

In yet another aspect, the ribozyme is an isolated enzymatic nucleic acid, which specifically cleaves mRNA transcribed from a nucleic acid encoding the chitinase-like molecule.

In a further aspect, the inflammatory disease is selected from the group consisting of asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema.

The invention includes a method of preventing an inflammatory disease in a mammal wherein the disease is associated with an increased level of a chitinase-like molecule. The method comprises administering an effective amount of a chitinase-like molecule inhibitor to the mammal, thereby preventing the inflammatory disease in the mammal.

In one aspect, the mammal is a human.

In another aspect, the chitinase-like molecule is selected from the group consisting of a YM-1, a YM-2, an acidic mammalian chitinase (AMCase), an oviductal glycoprotein 1, a cartilage glycoprotein 1, a chitotriosidase, a mucin 9, a cartilage glycoprotein-39, and a chondrocyte protein 39.

In another aspect, the chitinase-like molecule inhibitor is selected from the group consisting of a chemical compound, an antibody, a ribozyme, a nucleic acid, and an antisense nucleic acid molecule.

In a further aspect, the inflammatory disease is selected from the group consisting of asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema.

In yet another aspect, the chitinase-like molecule is a YM protein and further wherein the chitinase-like molecule inhibitor is selected from the group consisting of allosamidin, glucoallosamidin A, glucoallosamidin B, methyl-N-demethylallosamidin, demethylallosamidin, didemthylallosamidin, styloguanidine, a styloguanidine derivative, dipeptide cyclo-(L-Arg-D-Pro), dipeptide cyclo-(L-Arg-L-Pro), dipeptide cyclo-(D-Arg-D-Pro), dipeptide cyclo-(D-Arg-L-Pro), riboflavin, a flavin derivative, copper, zinc, and mercury.

In another aspect, the chitinase-like molecule is AMCase.

The invention includes a method of treating an inflammatory disease in a mammal wherein the disease is associated with an increased level of chitinase. The method comprising administering an effective amount of a chitinase inhibitor to the mammal, thereby treating the inflammatory disease in the mammal.

In one aspect, the mammal is a human.

In another aspect, the chitinase is acidic mammalian chitinase (AMCase) and the chitinase inhibitor is selected from the group consisting of a chemical compound, an antibody, a ribozyme, a nucleic acid, a nucleic acid, and an antisense nucleic acid molecule.

In yet another aspect, the chemical compound is selected from the group consisting of allosamidin, glucoallosamidin A, glucoallosamidin B, methyl-N-demethylallosamidin, demethylallosamidin, didemthylallosamidin, stylogaunidine, a styloguanidine derivative, dipeptide cyclo-(L-Arg-D-Pro), dipeptide cyclo-(L-Arg-L-Pro), dipeptide cyclo-(D-Arg-D-Pro), dipeptide cyclo-(D-Arg-L-Pro), riboflavin, a flavin derivative, copper, zinc, and mercury.

In one aspect, the antibody specifically binds with AMCase.

In another aspect, the antisense nucleic acid molecule is an isolated nucleic acid complementary to an isolated nucleic acid encoding an AMCase, or a fragment thereof.

In yet another aspect, the inflammatory disease is selected from the group consisting of asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema.

The invention includes a method for treating an inflammatory disease in a mammal wherein the disease is associated with an increased level of interleukin-13. The method comprises administering an effective amount of a chitinase-like molecule inhibitor to the mammal, thereby treating the inflammatory disease in a mammal.

In one aspect, the mammal is a human.

In another aspect, the chitinase-like molecule inhibitor is selected from the group consisting of a chemical compound, an antibody, a ribozyme, a nucleic acid, and an antisense nucleic acid molecule.

The invention also includes a method for treating an inflammatory disease in a mammal wherein the disease is associated with a Th2 inflammatory response. The method comprises administering an effective amount of a chitinase-like molecule inhibitor to the mammal, thereby treating the inflammatory disease in a mammal.

The invention includes a method of identifying a compound useful for treating an inflammatory disease in a mammal. The method comprises administering a compound to a mammal afflicted with an inflammatory disease and comparing the level of a chitinase-like molecule in the mammal with the level of the chitinase-like molecule in the mammal prior to administration of the compound, wherein a lower level of the chitinase-like molecule in the mammal after administration of the compound compared with the level of the chitinase-like molecule in the mammal prior to administration of the compound is an indication that the compound is useful for treating an inflammatory disease in the mammal, thereby identifying a compound useful for treating an inflammatory disease. In one aspect, the invention includes a compound identified using this method.

In one aspect, the level of a chitinase-like molecule is selected from the group consisting of the level of chitinase-like molecule nucleic acid expression and the level of chitinase-like molecule enzymatic activity.

In another aspect, the chitinase-like molecule is selected from the group consisting of a YM-1, a YM-2, an acidic mammalian chitinase (AMCase), an oviductal glycoprotein 1, a cartilage glycoprotein 1, a chitotriosidase, a mucin 9, a cartilage glycoprotein-39, and a chondrocyte protein 39.

In yet another aspect, the mammal is a mouse.

In a further aspect, the mouse is selected from the group consisting of a transgenic mouse constitutively expressing interleukin 13 and a transgenic mouse inducibly expressing interleukin 13.

In another aspect, the chitinase-like molecule is AMCase. In yet another aspect, the invention includes a compound identified using this method.

The invention includes a method of identifying a compound useful for treating an inflammatory disease. The method comprises contacting a cell with a compound and comparing the level of a chitinase-like molecule in the cell with the level of the chitinase-like molecule in an otherwise identical cell not contacted with the compound, wherein a lower level of the chitinase-like molecule in the cell contacted with the compound compared with the level of the chitinase-like molecule in the cell not contacted with the compound is an indication that the compound is useful for treating an inflammatory disease, thereby identifying a compound useful for treating an inflammatory disease.

The invention includes a kit for treating an inflammatory disease in a mammal wherein the disease is associated with an increased level of a chitinase-like molecule. The kit comprises an effective amount of a chitinase-like molecule inhibitor, and further comprises an applicator and an instructional material for the use thereof.

In one aspect, the chitinase-like molecule inhibitor is selected from the group consisting of a chemical compound, an antibody, a ribozyme, an antisense molecule, and a nucleic acid.

In another aspect, the chemical compound is selected from the group consisting of allosamidin, glucoallosamidin A, glucoallosamidin B, methyl-N-demethylallosamidin, demethylallosamidin, didemthylallosamidin, stylogaunidine, a styloguanidine derivative, dipeptide cyclo-(L-Arg-D-Pro), dipeptide cyclo-(L-Arg-L-Pro), dipeptide cyclo-(D-Arg-D-Pro), dipeptide cyclo-(D-Arg-L-Pro), riboflavin, a flavin derivative, copper, zinc, and mercury.

In yet another aspect, the chitinase-like molecule is AMCase.

The invention includes a kit for preventing an inflammatory disease in a mammal wherein the disease is associated with an increased level of a chitinase-like molecule. The kit comprises an effective amount of an chitinase-like molecule inhibitor, and further comprises an applicator and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIG. 2A (transgene (−), 100×) and FIG. 2B (transgene (+), 100×) illustrate histologic tissue from the control and CC10Il-13 mice respectively. FIG. 2B demonstrates the eosinophil, lymphocyte, and macrophage rich inflammation in the parenchyma of the IL-13 overexpressing mice. FIG. 2C (transgene (−), 250×) and FIG. 2D (transgene (+), 250×) compare the airway epithelial cells of control normal mice and CC10-IL-13 transgenic mice respectively. FIG. 2D illustrates the epithelial hypertrophy in the airways of mice overexpressing IL-13.

FIG. 3, comprising FIG. 3A depicts airways from transgene (−) mice, and FIG. 3B depicts mucus metaplasia and goblet cell hyperplasia in transgene (+) mice. Magnification is 100×.

FIG. 4, comprising FIG. 4A depicts collagen deposition in transgene (−) mice. FIG. 4B depicts enhanced collagen deposition in transgene (+) mice.

FIG. 6, comprising FIGS. 6A through 6E, depicts histologic and morphometric analysis of lungs from CC10-rtTA-IL-13 inducible mice. Lungs were removed, fixed to pressure, and processed for microscopy to show alveolar enlargement upon transgene induction after dox administration. FIG. 6A depicts inducible transgene (+) mice before dox administration. FIG. 6B depicts inducible transgene (+) mice one day after dox administration. FIG. 6C depicts inducible transgene (+) mice alveoli 1 week after dox administration, and FIG. 6D shows considerable alveolar enlargement in inducible transgene (+) mice 1 month after dox administration. FIG. 6E is a graph depicting the morphometric analysis of inducible transgene (+) mice. Four week old transgene (−) and (+) mice were randomized to normal or dox water and maintained on these treatments for one month. Lungs were removed, fixed to pressure, and chord length measurements were taken. Chord lengths were significantly larger in transgene (+) mice given dox than in transgene (−) mice given dox or transgene (+) mice given normal water.

FIG. 7 depicts crystal deposition in transgenic mice constitutively expressing IL-13. Crystals were multi-faceted and often needle-shaped.

FIG. 10, comprising In FIG. 10A, lungs were removed, after one month of randomization, total lung RNA was isolated, and YM gene expression was determined using RT-PCR. FIG. 10B depicts YM mRNA after dox or normal water administration for the indicated time intervals (w=week, m=month). mRNA levels were normalized using β-actin as a control.

FIG. 11, comprising FIG. 11A through FIG. 11H, depicts in situ hybridization of lung tissue from CC10-IL-13 and control mice to detect expression of YM in the tissues. FIG. 11A and FIG. 11B depict lung tissue from transgene (+) mice probed with antisense and sense probes, respectively. FIG. 11C and FIG. 11D depict lung tissue from transgene (−) mice with antisense and sense probes, respectively. FIG. 11E and FIG. 11F depict lung tissue from four week old transgene (+) mice probed using antisense and sense probes, respectively. FIG. 11G and FIG. 11H depict lung tissue from 10 week old transgene (+) mice probed with antisense and sense probes, respectively.

FIG. 13, comprising FIG. 13A and FIG. 13B, depicts acidic mammalian chitinase (AMCase) expression and chitinase activity in CC10-rtTA-IL-13 mice, respectively. FIG. 13A depicts the levels of mRNA encoding AMCases in lungs from transgene (−) and (+) mouse lungs that were placed on dox or normal water at one month of age and kept on this regimen for the noted intervals. AMCase and β-actin expression were evaluated by RT-PCR. FIG. 13B is a graph depicting chitinase activity in inducible transgene (+) and (−) animals randomized to normal or dox water at one month of age. BAL fluid chitinase activity was assessed at the noted intervals after dox or normal water administration.

FIG. 14, comprising FIG. 14A and FIG. 14B depicts transgene (+) mouse lung tissue using antisense and sense probes, respectively. FIG. 14C and FIG. 14D depict transgene (−) mouse lung tissue using antisense and sense probes, respectively.

FIG. 15, comprising FIG. 15A depicts YM mRNA expression at the noted intervals after OVA aerosol challenge (d=days, h=hours). FIG. 15B depicts AMCase mRNA expression at the noted intervals after OVA aerosol challenge. FIG. 15C depicts the significantly (*$p<0.01$) higher chitinase activity detected in bronchoalveolar lavage fluids (BAL) from wild type mice twenty-four hours and later after OVA aerosol challenge.

FIG. 16, comprising FIGS. 16A through 16G, depict the effects of allosamidin (allos) on OVA sensitized and subsequently challenged wild type animals. FIG. 16A is a graph depicting the effect of daily allosamidin administration (1 mg/kg) on total BAL cell recovery. Asterisks indicate significant ($p<0.01$) reduction in total BAL cell recovery after allosamidin administration. FIG. 16B is a graph depicting the effect of daily allosamidin administration (1 mg/kg) on the percentage of eosinophils recovered in BAL fluid. Asterisks indicate significant ($p<0.01$) reduction in the percentage of eosinophils recovered after allosamidin administration. FIG. 16C is a graph depicting the effect of daily allosamidin administration (11 mg/kg) on the total number of eosinophils recovered in BAL fluid. Asterisks indicate significant ($p<0.01$) reduction in total eosinophil recovery after allosamidin administration. FIG. 16D is a graph depicting the effect of daily allosamidin administration (1 mg/kg) on the number of lymphocytes recovered in BAL fluid. Asterisks indicate significant ($p<0.01$) reduction in total lymphocyte recovery after allosamidin administration. FIG. 16E is a graph depicting the dose dependent effect of allosamidin on total BAL cell recovery. Daily allosamidin doses were given starting on Day one, and animals were evaluated for total BAL cell recovery on Days two and seven following OVA aerosol challenge. Asterisks indicate significant ($p<0.01$) reduction in total BAL cell recovery after allosamidin administration. FIG. 16F is a graph depicting the dose-dependent effect of allosamidin on the percentage eosinophil recovery in BAL. Asterisks indicate significant ($p<0.01$) reduction in percentage of eosinophils in BAL cell recovery after allosamidin administration. FIG. 16G is a graph depicting the dose-dependent effect of allosamidin on the total eosinophil recovery in BAL. Asterisks indicate significant ($p<0.01$) reduction in total eosinophil BAL cell recovery after allosamidin administration.

FIG. 17A through FIG. 17D, depicts the effects of allosamidin administration (randomized to 1 mg/kg allosamidin or vehicle control, daily doses intraperitoneally (i.p.) for 14 days) on five week old CC10-IL-13 transgene (+) and (−) mice. FIG. 17A is a graph depicting the effect of allosamidin administration on total BAL cell recovery. FIG. 17B is a graph depicting the effect of allosamidin administration on BAL eosinophil recovery. Asterisks indicate significant ($p<0.01$) decreases in eosinophil recovery. FIG. 17C is a graph depicting the effect of allosamidin administration on BAL lymphocyte recovery. Asterisks indicate significant ($p<0.01$) decreases in lymphocyte recovery. FIG. 17D is a graph depicting the effect of allosamidin administration on lung size. Lungs were removed, fixed to pressure, and assessed using volume displacement methodology as described elsewhere herein.

FIG. 18, comprising FIG. 18A is a graph depicting the effect of anti-AMCase antibodies on total ovalbumin-induced BAL cell counts. Comparisons between unchallenged (unchall) and mice that were sensitized to ovalbumin and challenged on three successive days with ovalbumin were made at a seven day time point. The mice were treated with 0.5 ml of anti-AMCase antibodies or control serum (serum) intraperitoneally every other day starting the day before the first aerosol exposure. FIG. 18B is a graph depicting the effect of anti-AMCase antibodies on the percentage of eosinophils in BAL fluids from our sensitized and challenged mice. Comparisons between unchallenged (unchall) and mice that were sensitized to ovalbumin and challenged on three successive days with ovalbumin were made at a seven day time point. The mice were treated with 0.5 ml of anti-AMCase antibodies or control serum (serum) intraperitoneally every other day starting the day before the first aerosol exposure.

FIG. 19 comprises FIGS. 19A through 19F.

DETAILED DESCRIPTION OF THE INVENTION

Figure 1:
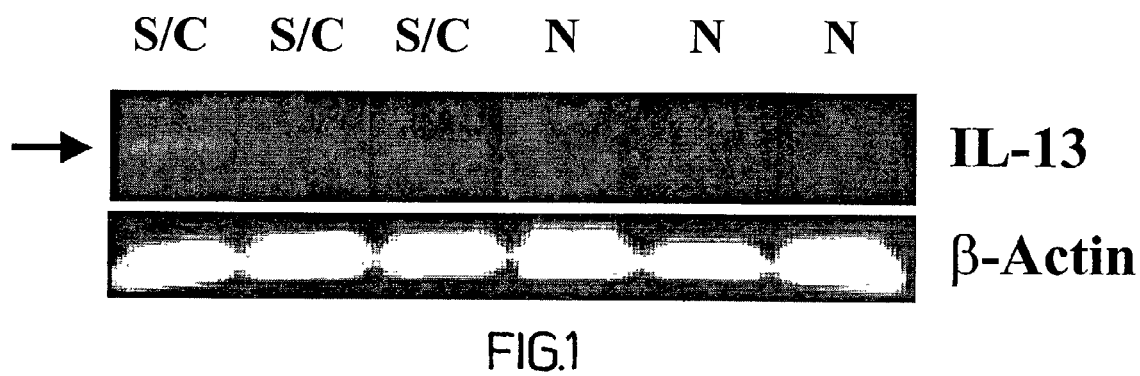
FIG. 1 depicts the levels of IL-13 mRNA from autopsy lung tissues from smokers who died of COPD (S/C) and non-smokers without COPD (N), as determined by RT-PCR. The arrow indicates IL-13 transcripts.

The invention includes a method of treating an inflammatory disease in a mammal where the disease is associated with, or mediated by, expression of a chitinase-like molecule. The method comprises administering a chitinase-like molecule inhibitor to the mammal. As the data disclosed elsewhere herein demonstrate, increased level of a chitinase-like molecule, is associated with, and/or mediates an inflammatory disease including, but not limited to, asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, emphysema, and the like.

The data disclosed herein demonstrate that increased expression, presence and/or activity of a chitinase-like molecule is associated with and/or mediates various inflammatory disease-associated etiologies including, but not limited to, tissue inflammation, increased lung volume, increased eosinophils in bronchoalveolar lavage (BAL) fluid, increased lymphocytes in BAL fluid and tissues, increased total cells in BAL fluid, increased alveolus size, increased airway resistance, increased mucus metaplasia, increased mucin expression, increased parenchymal fibrosis, increased airway remodeling, increased subepithelial fibrosis, increased collagen deposition in airway tissue, epithelial hypertrophy in the lung tissue, focal organization of crystalline material into Masson body-like fibrotic foci, and the like.

The data disclosed herein demonstrate, surprisingly, that even though some chitinase-like molecules, for example, YM, do not have detectable classical chitinase activity, administering a chitinase-like molecule inhibitor, such as, but not limited to, allosamidin, provides a therapeutic benefit and treats the disease. Further, the data disclosed herein demonstrate, for the first time, that administration an inhibitor of a chitinase-like molecule, e.g., an antibody to AMCase, provides a therapeutic effect and treats the disease. Indeed, the data demonstrate that administration of a chitinase-like molecule inhibitor before onset of the disease state serves to prevent the disease. Accordingly, the present invention provides a novel method whereby administration of a chitinase-like molecule inhibitor in a mammal afflicted with an inflammatory disease treats and/or prevents the disease when the disease is mediated by, or associated with, a chitinase-like molecule, even though the chitinase-like molecule may or may not have detectable chitinase activity.

Definitions:

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, an intravenous infusion, topical cream and the like, for administering the chitinase-like molecule inhibitor chemical compound, an antibody, nucleic acid, protein, and/or composition of the invention to a mammal.

"Chitinase," as used herein, refers to a family of polypeptides comprising microbial and mammalian chitinases. A chitinase of the present invention demonstrates detectable chitinase activity, in that it specifically cleaves chitin in an endochitinase manner.

"Chitinase-like molecule", as the term is used herein, encompasses a family of polypeptides comprising proteins that are defined by a certain degree of homology to known chitinases, but may not demonstrate detectable chitinase activity. Chitinase-like molecules include, but are not limited to acidic mammalian chitinase (also referred to as eosinophil chemotactic cytokine and exemplified by GenBank Acc. No. AF290003 and No. AF29004), YM1 (also known as chitinase 3-like 3, ECF-L precursor, as exemplified by GenBank Acc. No. M94584), YM2 as exemplified by GenBank Acc. No. AF461142, oviductal glycoprotein 1 as exemplified by GenBank Acc. No. XM_131100, cartilage glycoprotein 1 (also referred to as BRP-39, chitinase 3-like 1, GP-39, YKL-40 and exemplified by GenBank Acc. No. X93035), chitotriosidase as exemplified by GenBank Acc. No. NM_003465, oviductal glycoprotein 1 (also referred to as mucin 9, oviductin and as exemplified by GenBank Acc. No. NM_002557), cartilage glycoprotein-39 (also known as chitinase 3-like 1, GP-39, YKL-40, as exemplified by GenBank Acc. No. NM_001276), and chondrocyte protein 39 (also known as chitinase 3-like 2, YKL-39, as exemplified by GenBank Acc. No. NM_004000). Thus, the skilled artisan would appreciate, once armed with the teachings provided herein, that the present invention encompasses chitinase-like molecules that possess detectable chitinase activity as well as those similar to the afore-mentioned molecules in that the potential chitinase-like molecules shares substantial sequence homology to the family of proteins. The invention is not limited to these particular chitinase-like molecules; rather, the invention includes other chitinase-like molecules that share substantial homology with them and/or which possess detectable chitinase activity, and encompasses such molecules known in the art as well as those discovered in the future.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment" as applied to a nucleic acid, may ordinarily be at least about 20 nucleotides in length, typically, at least about 50 nucleotides, more typically, from about 50 to about 200 nucleotides, preferably, at least about 200 to about 300 nucleotides, even more preferably, at least about 300 nucleotides to about 400 nucleotides, yet even more preferably, at least about 400 to about 500, even more preferably, at least about 500 nucleotides to about 600 nucleotides, yet even more preferably, at least about 600 to about 700, even more preferably, at least about 700 nucleotides to about 800 nucleotides, yet even more preferably, at least about 800 to about 900, even more preferably, at least about 900 nucleotides to about 1000 nucleotides, yet even more preferably, at least about 1000 to about 1100, even more preferably, at least about 1100 nucleotides to about 1200 nucleotides, yet even more preferably, at least about 1200 to about 1300, even more preferably, at least about 1300 nucleotides to about 1400 nucleotides, yet even more preferably, at least about 1400 to about 1500, at least about 1500 to about 1550, even more preferably, at least about 1550 nucleotides to about 1600 nucleotides, yet even more preferably, at least about 1600 to about 1620 and most preferably, the nucleic acid fragment will be greater than about 1625 nucleotides in length.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 75% homology.

By "chitinase-like molecule inhibitor" is meant a compound that detectably inhibits the level of a chitinase-like molecule in a cell or tissue when compared to the level of the chitinase-like molecule in an otherwise identical cell or tissue in the absence of the compound. The level of the chitinase-like molecule includes, but is not limited to, the level of expression of a nucleic acid encoding the molecule, the level of chitinase-like molecule detectable, and/or the level of chitinase activity. Chitinase-like molecule inhibitors include, but are not limited to, a chemical compound (e.g., allosamidin, glucoallosamidin A, glucoallosamidin B, methyl-N-demethylallosamidin, demethylallosamidin, didemthylallosamidin, stylogaunidine, a styloguanidine derivative, dipeptide cyclo-(L-Arg-D-Pro), dipeptide cyclo-(L-Arg-L-Pro), dipeptide cyclo-(D-Arg-D-Pro), dipeptide cyclo-(D-Arg-L-Pro), riboflavin, a flavin derivative), copper, zinc, mercury, an antibody, a ribozyme, an antisense molecule, and a nucleic acid.

An "AMCase inhibitor," as the term is used herein, includes a chitinase-like molecule inhibitor, as defined previously, that inhibits AMCase. Such inhibitor includes, but it not limited to, a chemical compound, as well as a ribozyme, antisense molecule, an antibody, and the like, that inhibits the level of AMCase expression and/or activity in a cell or tissue compared with the level of AMCase expression and/or activity in the cell or tissue in the absence of the inhibitor, or in an otherwise identical cell or tissue, in the absence of the inhibitor. The inhibitor includes, but is not limited to, a chemical compound, a ribozyme, an antisense nucleic acid molecule, an antibody, and the like.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

As used herein, an "instructional material" includes a publication, a recording, a diagram, or any other medium of expression, which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container, which contains the nucleic acid, peptide, chemical compound and/or composition of the invention or be shipped together with a container, which contains the nucleic acid, peptide, chemical composition, and/or composition. Alternatively, the instructional material may be shipped separately from the container with the intention that the instructional material and the compound be used cooperatively by the recipient.

An "inflammatory disease" is used herein to refer to a state in which there is a response to tissue damage, cell injury, an antigen, and/or an infectious disease. In some cases, causation will not be able to be established. The symptoms of inflammation may include, but are not limited to cell infiltration and tissue swelling. Disease states contemplated under the definition of inflammatory disease include asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

"Constitutive" expression is a state in which a gene product is produced in a living cell under most or all physiological conditions of the cell.

"Inducible" expression is a state in which a gene product is produced in a living cell in response to the presence of a signal in the cell.

A "recombinant polypeptide" is one, which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

As used herein, the term "transgenic mammal" means a mammal, the germ cells of which, comprise an exogenous nucleic acid.

As used herein, to "treat" means reducing the frequency with which symptoms of the inflammatory disease, are experienced by a patient, or altering the natural history and/or progression of the disease in a patient.

As used herein, the term "antisense oligonucleotide" means a nucleic acid polymer, at least a portion of which is complementary to a nucleic acid which is present in a normal cell or in an affected cell. Most preferably, the antisense oligonucleotides comprise between about fifteen and about fifty nucleotides. The antisense oligonucleotides of the invention include, but are not limited to, phosphorothioate oligonucleotides and other modifications of oligonucleotides.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "portion" of a polynucleotide means at least at least about fifteen to about fifty sequential nucleotide residues of the polynucleotide. It is understood that a portion of a polynucleotide may include every nucleotide residue of the polynucleotide.

By the term "specifically binds," as used herein, is meant an antibody which recognizes and binds a chitinase-like molecule, but does not substantially recognize or bind other molecules in a sample.

A "prophylactic" treatment is a treatment administered to a subject who does not exhibit signs of a disease or exhibits only early signs of the disease for the purpose of decreasing the risk of developing pathology associated with the disease.

"Preventing" a disease, as the term is used herein, means that the onset of the disease is delayed, and/or that the symptoms of the disease will be decreased in intensity and/or frequency, when a chitinase-like molecule is administered compared with the onset and/or symptoms in the absence of the inhibitor.

A "therapeutic" treatment is a treatment administered to a subject who exhibits signs of pathology for the purpose of diminishing or eliminating those signs.

I. Methods

A. Methods of Treating an Inflammatory Disease

The present invention includes a method of treating an inflammatory disease wherein the disease is associated with an increased level of a chitinase-like molecule. Contemplated in the present invention are methods of treating an inflammatory disease in a mammal, preferably a human, using a chitinase-like molecule inhibitor. This is because, as would be appreciated by one skilled in the art when provided with the disclosure herein, inhibiting the expression and/or activity of a chitinase-like molecule serves as a treatment for inflammatory diseases, including diseases mediated by IL-13. That is, the data disclosed herein demonstrate that administration of a chitinase-like molecule inhibitor in a model of inflammatory disease associated with, or mediated by, expression of IL-13, treats the disease after it has become established. Further, the present invention relates to the discovery that chitinase-like molecules and chitinase-like molecule mRNA are present in increased levels in inflammatory disease tissue compared with the level of a chitinase-like molecule in normal tissue. Thus, the present invention relates to treating of such diseases using a chitinase-like molecule inhibitors, including, but not limited to, a chitinase-like molecule inhibitor (e.g., allosamidin).

Surprisingly, a chitinase-like molecule inhibitor can be administered to treat the disease even when there is no detectable chitinase activity. Thus, the skilled artisan would appreciate, based upon the disclosure provided herein, that the present invention is not limited to treatment of a disease where detectable chitinase activity is present; instead, the present invention encompasses treatment of a disease associated with or mediated by expression of a chitinase-like molecule even when there is no detectable chitinase activity.

It would be understood by one skilled in the art, based upon the disclosure provided herein, that inhibition of a chitinase-like molecule encompasses inhibition of a chitinase-like molecule expression, such as that mediated by, among other things, a ribozyme and/or antisense molecule that inhibits expression of a nucleic acid encoding a chitinase-like molecule. Additionally, the skilled artisan would appreciate, once armed with the teachings of the present invention, that inhibition of a chitinase-like molecule includes inhibition of a chitinase-like molecule activity in a cell. Such inhibition of a chitinase-like molecule activity can be effected using inhibitors of chitinase enzymatic activity, including, inter alia, allosamidin, 1,10-phenanthroline, glucoallosamidin A, glucoallosamidin B, methyl-N-demethylallosamidin, demethylallosamidin, didemthylallosamidin, stylogaunidine, a styloguanidine derivative, dipeptide cyclo-(L-Arg-D-Pro), dipeptide cyclo-(L-Arg-L-Pro), dipeptide cyclo-(D-Arg-D-Pro), dipeptide cyclo-(D-Arg-L-Pro), riboflavin, a flavin derivative, copper, zinc, mercury and the like. Further, inhibitors of chitinase-like molecule activity include an antibody that specifically binds with a chitinase-like molecule thereby preventing the enzyme from functioning. Thus, a chitinase-like molecule inhibitor includes, but is not limited to, inhibiting transcription, translation, or both, of a nucleic acid encoding a chitinase-like molecule; and it also includes inhibiting any activity of the peptide as well, including, but not limited to, the ability to cleave chitin.

The present invention includes a method of treating or preventing an inflammatory disease in a mammal. The method comprises administering a chitinase-like molecule inhibitor to a mammal in need of such treatment. This is because, as would be appreciated by one skilled in the art armed with the teachings of the present invention, inhibiting a chitinase-like molecule is useful for treating or preventing an inflammatory disease. Inhibition of a chitinase-like molecule prevents, in turn, the pathology associated with an inflammatory disease, as amply demonstrated by the data disclosed herein.

More specifically, the invention relates to inhibiting a chitinase-like molecule using various inhibitors. That is, one skilled in the art would understand, based upon the disclosure provided herein, that compounds that inhibit the expression, activity, and/or function of a chitinase-like molecule encompass, but are not limited to, an antibody, an antisense nucleic acid, a ribozyme, a small molecule, a peptidomimetic and a chemical compound, either known or to be developed, which inhibits a chitinase-like molecule, and thereby an inflammatory disease.

The invention encompasses inhibition of a chitinase-like molecule where the molecule does or does not demonstrate detectable chitinase activity in vitro or in vivo. That is, without wishing to be bound by any particular theory, whether the chitinase-like molecule demonstrates detectable chitinase activity, either in a cell or tissue or in a cell-free system, is not relevant. More specifically, as demonstrated by the data disclosed herein, a chitinase-like molecule, such as Ym, which does not demonstrate detectable chitinase activity in vitro or in vivo, is expressed at an increased level in disease cells and tissues compared to a cell or tissue that does not demonstrate inflammatory disease pathology, and inhibiting Ym using, inter alia, allosamidin, treats and/or prevents the disease. Additionally, the data disclosed herein further demonstrate that increased level of a chitinase, AMCase, in a cell or tissue is associated with, or mediates, an inflammatory disease. Moreover, inhibition of AMCase treats the disease. Such therapeutic effect may be related to inhibition of undetectable chitinase activity, or it may be that the therapeutic effect does not relate to any chitinase or chitinase-like activity of the chitinase-like molecule, and the skilled artisan, based upon the disclosure provided herein, would appreciate that the therapeutic effect can be, but need not be, correlated with any chitinase activity by the molecule.

One skilled in the art would appreciate, based on the disclosure provided herein, that an inhibitor of the invention includes molecules and compounds that prevent or inhibit the expression, activity or function of a chitinase-like molecule in a mammal. That is, the invention contemplates that an antisense and/or antisense molecule that inhibits, decreases, and/or abolishes expression of a chitinase-like molecule such that the chitinase-like molecule is not detectable in the cell or tissue is an inhibitor of the invention. For instance, a compound that degrades a chitinase-like molecule can decrease its function, and can be an inhibitor as contemplated in the present invention.

Inhibition of a chitinase-like molecule can be assessed using a wide variety of methods, including those disclosed herein, as well as methods well-known in the art or to be developed in the future. That is, the routineer would appreciate, based upon the disclosure provided herein, that inhibition of chitinase-like molecule expression can be readily assessed using methods that assess the level of a nucleic acid encoding a chitinase-like molecule (e.g., mRNA) and/or the level of a chitinase-like molecule present in a cell or fluid. Moreover, the routineer would understand that inhibition of a chitinase-like molecule can be assessed by determining the inhibition of chitinase enzymatic activity in a cell or bodily fluid as exemplified elsewhere herein and/or using methods well-known in the art or to be developed in the future.

One skilled in the art, based upon the disclosure provided herein, would understand that the invention encompasses treatment of a variety of inflammatory diseases, including, but not limited to, asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema, and the like. As disclosed herein, these diseases involve and/or are mediated by, increased chitinase-like molecules in tissues where increased chitinase-like molecules includes, and is not limited to, increased chitinase-like molecule expression, increased chitinase-like molecule activity, or both.

Further, the skilled artisan would further appreciate, based upon the teachings provided herein, that the diseases encompass any disease comprising increased chitinase-like molecule in a tissue including, among others, a disease mediated by increased IL-13 and/or increased IL-4 production. This is because, as more fully set forth elsewhere herein, the data disclosed herein demonstrate that increased IL-13 and/or increased IL-4 mediates an increase in chitinase-like molecules which, in turns, mediates and/or is associated with a variety of changes associated with inflammatory disease including, but not limited to, tissue inflammation, increased lung volume, increased eosinophils in bronchioalveolar lavage (BAL) fluid, increased lymphocytes in BAL fluid, increased total cells in BAL fluid, increased alveolus size, increased deposition of crystals comprising chitinase-like molecules in lung tissue, increased airway resistance, increased mucus metaplasia, increased mucin expression, increased parenchymal fibrosis, increased airway remodeling, increased subepithelial fibrosis, increased collagen deposition in airway tissue, epithelial hypertrophy in the lung tissue, focal organization of crystalline material into Masson body-like fibrotic foci, and the like.

Therefore, the data disclosed herein demonstrate that inhibition of a chitinase-like molecule in a mammal afflicted with an inflammatory disease, wherein the disease is mediated by and/or associated with increased expression of IL-13 and/or IL-4, will treat the disease by mediating a decrease in the level of a chitinase-like molecule which, in turn, treats the disease. For instance, such data include, but are not limited to, the inhibition of various tissue pathology by administering a chitinase-like molecule inhibitor (e.g., allosamidin) to a mammal where increased expression of IL-13 mediates increased chitinase-like molecule activity and increased chitinase-like molecule expression.

The present invention further comprises a method for treating an inflammatory disease mediated by and/or associated with a Th2 inflammatory response in a mammal. The skilled artisan, when armed with the present disclosure and the teachings provided herein, would understand that an inflammatory disease mediated by and/or associated with a Th2 inflammatory response encompasses a variety of inflammatory diseases, including, but not limited to, asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema, and the like. As disclosed herein, these diseases are mediated by a Th2 inflammatory response in an mammal, and result in, among other things, increased IL-13 production and/or expression, increased chitinase-like molecule activity and/or expression, and the like. Increased chitinase-like molecules include, but is not limited to, increased chitinase-like molecule expression, increased chitinase-like molecule activity, or both.

Further, the skilled artisan would appreciate, based upon the teachings provided herein, that the diseases encompass any disease comprising increased chitinase-like molecule in a tissue including, among others, a disease mediated by increased Th2 inflammatory response. This is because, as more fully set forth elsewhere herein, the data disclosed herein demonstrate that increased Th2 inflammatory responses result in, inter alia, increased IL-13 and/or increased IL-4 activity and/or expression, an increase in chitinase-like molecules which, in turns, mediates and/or is associated with a variety of changes associated with inflammatory disease including, but not limited to, increased total cells in BAL fluid, increased alveolus size, increased deposition of crystals comprising chitinase-like molecules in lung tissue, increased airway resistance, increased mucus metaplasia, increased mucin expression, increased parenchymal fibrosis, increased airway remodeling, increased subepithelial fibrosis, increased eosinophils in bronchioalveolar lavage (BAL) fluid, increased lymphocytes in BAL fluid, and the like.

Therefore, the data disclosed herein demonstrate that inhibition of a chitinase-like molecule in a mammal afflicted with an inflammatory disease, wherein the disease is mediated by and/or associated with an increased Th2 inflammatory response, will treat the disease by mediating a decrease in the level of a chitinase-like molecule which, in turn, treats the disease. For instance, such data include, but are not limited to, the inhibition of various tissue pathology by administering a chitinase-like molecule inhibitor (e.g., allosamidin) to a mammal where a Th2 inflammatory response mediates increased chitinase-like molecule activity and increased chitinase-like molecule expression.

The skilled artisan will further appreciate that a chitinase-like molecule is a molecule that exhibits a substantial degree of homology to known chitinases, such that it has been or can be classified as a chitinase family molecule based upon, inter alia, its amino acid sequence. Further, the skilled artisan would understand, based upon the disclosure provided herein, that while a chitinase-like molecule can exhibit homology to a known chitinase, a chitinase-molecule need not demonstrate detectable chitinase activity, in that they may not detectably cleave chitin an in assay known in the art. Such chitinase like molecules include, but are not limited to, acidic mammalian chitinase (eosinophil chemotactic cytokine), YM1 (chitinase 3-like 3, ECF-L precursor), YM2. oviductal glycoprotein 1, cartilage glycoprotein 1 (BRP-39, chitinase 3-like 1, GP-39, YKL-40), chitotriosidase, oviductal glycoprotein 1 (mucin 9, oviductin), cartilage glycoprotein-39 (chitinase 3-like 1, GP-39, YKL-40), and chondrocyte protein 39 (chitinase 3-like 2, YKL-39).

A chitinase-like molecule inhibitor can include, but should not be construed as being limited to a chemical compound, a protein, a peptidomemetic, an antibody, a ribozyme, and an antisense nucleic acid molecule.

One of skill in the art would readily appreciate, based on the disclosure provided herein, that a chitinase-like molecule inhibitor encompasses a chemical compound that inhibits the activity of a chitinase-like molecule. Chitinase-like molecule inhibitors are well known in the art, and some of the key critical elements of one class of chitinase-like molecule inhibitors have been defined (Spindler and Spindler-Barth, 1999, Chitin and Chitinases, Birkhauser Verlag Basel, Switzerland). Additionally, a chitinase-like molecule inhibitor encompasses a chemically modified compound, and derivatives, as is well known to one of skill in the chemical arts.

The skilled artisan would appreciate that a chitinase-like molecule inhibitor encompasses an already known chitinase-like molecule inhibitor such as, but not limited to, allosamidin (Allosamidine, Carbohydrate Chemistry Industrial Research Limited, Lower Hutt, New Zealand, and Eli Lilly and Co., Greenfield, Ind.) and its derivatives (see, e.g., U.S. Pat. No. 5,413,991), glucoallosamidin A, glucoallosamidin B, methyl-N-demethylallosamidin (Nishimoto et al., 1991, J. Antibiotics 44:716–722) demethylallosamidin (U.S. Pat. No. 5,070,191), and didemthylallosamidin (Zhou et al., 1993, J. Antibiotics 46:1582–1588). Further contemplated chitinase-like molecule inhibitors include stylogaunidine and its derivatives (Kato et al., 1995, Tetrahedron. Lett. 36:2133–2136), dipeptide cyclo-(L-Arg-D-Pro) (Izumida et al., 1996, J. Antibiotics 49:76–80), divalent cations (e.g., $Cu^{2+}$, $Zn^{2+}$, and $Hg^{2+}$) (Izumida et al., 1995, J. Mar. Biotechnol. 2:163–166; Funke and Spindler, 1989, Comp. Biochem Physiol. 94B:691–695), and riboflavin and flavin derivatives (International Publication No. WO 02/23991).

Further, one of skill in the art would, when equipped with this disclosure and the methods exemplified herein, appreciate that a chitinase-like molecule inhibitor includes such inhibitors as discovered in the future, as can be identified by well-known criteria in the art of pharmacology, such as the physiological results of inhibition of a chitinase-like molecule as described in detail herein and/or as known in the art. Therefore, the present invention is not limited in any way to any particular chitinase-like molecule inhibitor as exemplified or disclosed herein; rather, the invention encompasses those inhibitors that would be understood by the routineer to be useful as are known in the art and as are discovered in the future.

Further methods of identifying and producing a chitinase-like molecule inhibitor are well known to those of ordinary skill in the art, including, but not limited, obtaining an inhibitor from a naturally occurring source (i.e., *Streptomyces* sp., *Pseudomonas* sp., *Stylotella aurantium*). Alternatively, a chitinase-like molecule inhibitor can be synthesized chemically. Further, the routineer would appreciate, based upon the teachings provided herein, that a chitinase-like molecule inhibitor can be obtained from a recombinant organism. Compositions and methods for chemically synthesizing chitinase-like molecule inhibitors and for obtaining them from natural sources are well known in the art and are described in, among others, Yamada et al., U.S. Pat. Nos. 5,413,991, and 5,070,191.

The skilled artisan would also appreciate, based on the disclosure provided herein, that a chitinase-like molecule inhibitor encompasses an antibody that specifically binds with a chitinase-like molecule, for example, AMCase, thereby inhibiting the action of these proteins. For instance, antibodies that specifically bind to YM are well known to those of ordinary skill in the art (Webb et al., 2001, J. Biol. Chem. 276:41969–41976). Similarly, antibodies to chitinase-like molecules can be produced using standard methods disclosed herein or well known to those of ordinary skill in the art (Harlow et al., 1988, Antibodies: A Laboratory Manual, Cold Spring Harbor, N.Y.). Thus, the present invention is not limited in any way to any particular antibody; instead, the invention includes any antibody that specifically binds with a chitinase-like molecule either known in the art and/or identified in the future.

One of skill in the art will appreciate that an antibody can be administered as a protein, a nucleic acid construct encoding a protein, or both. Numerous vectors and other compositions and methods are well known for administering a protein or a nucleic acid construct encoding a protein to cells or tissues. Therefore, the invention includes a method of administering an antibody or nucleic acid encoding an antibody (e.g., synthetic antibody) that is specific for a chitinase-like molecule. (Sambrook et al., 1989, Molecular Cloning: A Laboratory Manual, Cold Spring Harbor Laboratory, New York; Ausubel et al., 1997, Current Protocols in Molecular Biology, John Wiley & Sons, New York).

The skilled artisan would understand, based upon the disclosure provided herein, that the invention encompasses administering an antibody that specifically binds with a chitinase-like molecule of interest, or a nucleic acid encoding the antibody, wherein the antibody molecule further comprises an intracellular retention sequence such that the antibody binds with the chitinase-like molecule and prevents its expression at the cell surface and/or its export from a cell. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11–17). Thus, the invention encompasses methods comprising inhibiting expression of a chitinase-like molecule on a cell and/or its secretion from a cell, where the skilled artisan would understand such inhibition would provide a benefit based upon the disclosure provided herein.

The present invention is not limited to chemical compounds and antibodies against a chitinase-like molecule. One of skill in the art would appreciate that inhibiting the expression of a polypeptide is like wise an effective method of inhibiting the activity and function of the polypeptide. Thus, a method is provided for the inhibition of a chitinase-like molecule by inhibiting the expression of a nucleic acid encoding a chitinase-like molecule. Methods to inhibit the expression of a gene are well known to those of ordinary skill in the art, and include the use of ribozymes or antisense oligonucleotide.

Antisense oligonucleotides are DNA or RNA molecules that are complementary to some portion of an mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931).

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a chitinase-like molecule can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence chitinase-like molecule, one of ordinary skill in the art could synthesize an antisense oligonucleotide or ribozyme without undue experimentation, provided with the disclosure and references incorporated herein.

One of skill in the art will appreciate that inhibitors of chitinase-like molecule gene expression can be administered singly or in any combination thereof. Further, chitinase-like molecule inhibitors can be administered singly or in any combination thereof in a temporal sense, in that they may be administered simultaneously, before, and/or after each other. One of ordinary skill in the art will appreciate, based on the disclosure provided herein, that chitinase-like molecule inhibitors to inhibit gene expression can be used to treat asthma, COPD, and other inflammatory diseases and that an inhibitor can be used alone or in any combination with another inhibitor to effect a therapeutic result.

B. Method of Preventing an Inflammatory Disease

It will be appreciated by one of skill in the art, when armed with the present disclosure including the methods detailed herein, that the invention is not limited to treatment of an inflammatory disease once the disease is established. Particularly, the symptoms of the disease need not have manifested to the point of detriment to the mammal; indeed, the disease need not be detected in a mammal before treatment is administered. That is, significant pathology from an inflammatory disease does not have to occur before the present invention may provide benefit. Therefore, the present invention, as described more fully herein, includes a method for preventing an inflammatory disease in a mammal, in that a chitinase-like molecule inhibitor, as discussed previously elsewhere herein, can be administered to a mammal prior to the onset of an inflammatory disease, thereby preventing the disease as demonstrated by the data disclosed herein.

One of skill in the art, when armed with the disclosure herein, would appreciate that the prevention of inflammatory disease encompasses administering to a mammal a chitinase-like molecule inhibitor as a preventative measure against inflammatory disease. As detailed herein, the symptoms and etiologies of chitinase-like molecule-associated inflammatory disease include tissue inflammation, increased lung volume, increased eosinophils in bronchioalveolar lavage (BAL) fluid, increased lymphocytes in BAL fluid, increased total cells in BAL fluid, increased alveolus size, increased deposition of crystals comprised of chitinase-like molecules in lung tissue, increased airway resistance, increased mucus metaplasia, increased mucin expression, increased parenchymal fibrosis, increased airway remodeling, increased subepithelial fibrosis, increased collagen deposition in airway tissue, epithelial hypertrophy in the lung tissue, focal organization of crystalline material into Masson body-like fibrotic foci, and the like. Given these etiologies and the methods disclosed elsewhere herein, the skilled artisan can recognize and prevent an inflammatory disease in a mammal using a chitinase-like molecule inhibitor before the disease pathology can be detected. This is because the data disclosed herein demonstrate that administration of a chitinase-like molecule inhibitor, including, but not limited to, allosamidin, prevented onset of an inflammatory disease in a mammal, whether the disease was induced by an allergen (e.g. ovalbumin sensitization) or whether the mammal was genetically predisposed to the disease (e.g., transgenic mice constitutively or inducibly overproducing IL-13). Accordingly, the skilled artisan would appreciate, based on the disclosure provided elsewhere herein, that the present invention includes a method of preventing disease comprising inhibiting a chitinase-like molecule using a chitinase-like molecule inhibitor. Further, as more fully discussed elsewhere herein, methods of inhibiting a chitinase-like molecule encompass a wide plethora of techniques for inhibiting not only chitinase-like molecule activity, but also for inhibiting expression of a nucleic acid encoding a chitinase-like molecule. Additionally, as disclosed elsewhere herein, one skilled in the art would understand, once armed with the teaching provided herein, that the present invention encompasses a method of preventing a wide variety of diseases where expression and/or activity of a chitinase-like molecule mediates the disease. Methods for assessing whether a disease relates to over expression or increased activity of a chitinase-like molecule are disclosed elsewhere herein and/or are well-known in the art. Further, the invention encompasses treatment or prevention of such diseases discovered in the future.

The invention further encompasses methods for treating an IL-13 mediated inflammatory disease. This is because, as the data disclosed herein demonstrate, IL-13 overexpression in the lungs, among other tissues, whether inducible or constitutive, mediates or is associated with the increased expression of chitinase-like molecule in respiratory tissues, leading to, among other things, the pathologies described elsewhere herein. Thereby, the present invention includes methods of treating an IL-13 mediated inflammatory disease using the methods of the present invention.

The invention encompasses administration of a chitinase-like molecule inhibitor to practice the methods of the invention; the skilled artisan would understand, based on the disclosure provided herein, how to formulate and administer the appropriate chitinase-like molecule inhibitor to a mammal. Indeed, the successful administration of chitinase-like molecule inhibitors have been extensively reduced to practice as exemplified herein. However, the present invention is not limited to any particular method of administration or treatment regimen. This is especially true where it would be appreciated by one skilled in the art, equipped with the disclosure provided herein, including the extensive reduction to practice using an art-recognized model of inflammatory disease, that methods of administering a chitinase-like molecule inhibitor can be readily determined by one of skill in the pharmacological arts.

More specifically, the data disclosed herein demonstrate that increased expression of IL-13 mediates or is correlated with increased level of a chitinase-like molecule (e.g., Ym, AMCase, and the like) and that inhibiting a chitinase-like molecule using, among other things, an antibody that specifically binds with the chitinase-like molecule, prevents, ameliorates, and/or treats inflammatory disease. That is, for instance, AMCase mRNA is expressed at a greater level in inflammatory disease cells and/or tissues and administration of antibody that specifically binds with AMCase treats the disease in an art-recognized animal model of inflammatory disease. Further, the data disclosed herein demonstrate similar results relating to expression of Ym and inhibition of Ym using a chemical compound, i.e., allosamidin, which is a known chitinase-like molecule inhibitor. The skilled artisan will appreciate that the present invention is not limited to these chitinase-like molecules or to these chitinase-like molecule inhibitors, and the data disclosed herein amply demonstrate that inhibition of a chitinase-like molecule can effectively treat and/or prevent an inflammatory disease.

As used herein, the term "pharmaceutically-acceptable carrier" means a chemical composition with which an appropriate chitinase-like molecule inhibitor may be combined and which, following the combination, can be used to administer the appropriate chitinase-like molecule inhibitor to a mammal.

The pharmaceutical compositions useful for practicing the invention may be administered to deliver a dose of between about 0.1 ng/kg/day and 100 mg/kg/day.

Pharmaceutical compositions that are useful in the methods of the invention may be administered systemically in oral solid formulations, ophthalmic, suppository, aerosol, topical or other similar formulations. In addition to the appropriate chitinase-like molecule inhibitor, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate chitinase-like molecule inhibitor according to the methods of the invention.

Compounds which are identified using any method described herein as potential useful compounds for treatment and/or prevention of a disease of interest can be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats and dogs, and birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 μg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

E. Methods of Identifying a Useful Compound

The invention encompasses a method for identifying a compound or intervention that treats an inflammatory disease. One skilled in the art would appreciate, based upon the disclosure provided herein, that assessing the expression and/or activity of a chitinase-like molecule can be performed by assessing, among other things, the levels of a chitinase-like molecule or the mRNA that encodes it in a cell or tissue, and the like, and then the level can be compared to the level in an otherwise identical cell or tissue to which the compound is not administered. Alternatively, the level of chitinase-like molecule or the mRNA that encode it in a cell or tissue contacted with a compound can be compared with the level of the chitinase-like molecule or its mRNA in the cell or tissue prior to administration of the compound. One skilled in the art would understand that such compound can be a useful potential therapeutic for treating and/or preventing an inflammatory disease, and for treating and preventing an IL-13 mediated inflammatory disease, and/or for treating a disease associated with and/or mediated by a Th2 inflammatory response.

The skilled artisan would further appreciate that the methods for identifying a compound useful for inhibiting a chitinase-like molecule include methods wherein a compound is administered to a cell, tissue, or animal. That is, the skilled artisan, when armed with the present disclosure, would recognize that the teachings herein can be used to identify a compound useful for inhibiting a chitinase-like molecule in a cell or tissue expressing a chitinase-like molecule. Such cells and tissues are well known in the art, and can include cells and tissues derived from a transgenic non-human animal having altered expression IL-13, IL-4, and/or a chitinase-like molecule, or a transgenic animal comprising an inflammatory disease, and/or a cell or tissue derived therefrom.

Additionally, a cell or tissue comprising expression of a chitinase-like molecule can be contacted with a compound and the level of the chitinase-like molecule can be assessed and compared to the level of the chitinase-like molecule in the cell and/or tissue prior to administration of the compound. Further, the level of the chitinase-like molecule can be compared to the level of the chitinase-like molecule in an otherwise identical cell or tissue not contacted with the compound.

One skilled in the art would appreciate, based upon the disclosure provided herein, that the cell or tissue can express endogenous chitinase-like molecule, but the invention further encompasses a cell or tissue that has been modified to express a chitinase-like molecule not otherwise expressed in the tissue, e.g., a nucleic encoding a chitinase-like molecule of interest can be introduced and expressed in the cell or tissue where it is not typically expressed, or is expressed at a different level than after the nucleic acid is introduced into the cell or tissue. Thus, the invention includes a wide plethora of assays, comprising a cell, tissue, or an animal, wherein the level of a chitinase-like molecule can be assessed in the presence or absence of a compound. Accordingly, the skilled artisan would be able to identify a compound using the methods disclosed herein and cell culture and cell propagation techniques well known in the art to assess the ability of a compound to affect the level of a chitinase-like molecule. Therefore, the present invention further encompasses a method of identifying a compound useful for inhibiting a chitinase-like molecule in a cell or tissue, as well as in an animal.

One of skill in the art would understand, based upon the disclosure provided herein, that the invention includes a method of identifying a compound useful for treating an inflammatory disease in a mammal. As would be understood by one skilled in the art armed with the teachings provided herein, the method encompasses identifying a compound that treats an inflammatory disease in a cell or tissue. The method comprises identifying a substance or compound that inhibits the expression and/or activity of a chitinase-like molecule in a mammal (including in a cell or tissue thereof), preferably in the respiratory tract. This is because, as discussed elsewhere herein, the data demonstrate that inhibiting the expression or activity of a chitinase-like molecule provides a therapeutic benefit thereby treating or preventing an inflammatory disease mediated by or associated with increased expression or activity of a chitinase-like molecule. This is because the present invention discloses, for the first time, that increased level of a chitinase-like molecule is associated with, or mediates, such disease and that inhibiting the chitinase-like molecule (e.g., YM, AMCase, and the like), using a chitinase-like molecule inhibitor (e.g., allosamidin, an antibody specific for the chitinase-like molecule, such as, but not limited to, an antibody that specifically binds with AMCase) prevents and/or treats the disease.

Thus, the skilled artisan, once armed with the teachings of the invention, would appreciate that a compound that inhibits a chitinase-like molecule is a powerful potential therapeutic or prophylactic treatment of inflammatory disease, such that identification of such a compound identifies a potential therapeutic for such disease.

The method comprises administering to a mammal afflicted with an inflammatory disease, a compound, and comparing the level of a chitinase-like molecule in the mammal before and after administration of the compound. The routineer would understand, based on the disclosure provided herein, that a lower level of a chitinase-like molecule or the mRNA that encodes it in the mammal after administration of the compound compared with the level of a chitinase-like molecule or its mRNA before administration of the compound indicates that the compound is useful for treating an inflammatory disease in a mammal.

This is because, as stated previously elsewhere herein, it has been discovered that inhibiting a chitinase-like molecule in an animal treats or prevents a disease associated with increased chitinase-like molecule expression and/or activity, e.g., an inflammatory disease with enhanced tissue remodeling and fibrosis. The skilled artisan would also appreciate, in view of the disclosure provided herein, that assays to determine the level of a chitinase-like molecule in a mammal, including a cell or tissue thereof, include those well known in the art, or those to be developed in the future, all of which can be used to assess the level of a chitinase-like molecule in a mammal (or cell or tissue thereof) before and after administration of the compound. The skilled artisan would further appreciate that the levels of a chitinase-like molecule, as disclosed elsewhere herein, include levels of chitinase-like molecule activity and levels of chitinase-like molecule expression. Further, the invention encompasses a compound identified using this method.

The invention further includes additional methods for identifying a compound useful for inhibiting a chitinase-like molecule and thereby an inflammatory disease in a mammal. More specifically, the method comprises assessing the level of a chitinase-like molecule expression, production, or activity in a mammal (or a cell or tissue thereof) to which the compound is administered in comparison to an identical mammal (or cell or tissue thereof) to which the compound is not administered. Additionally, the method comprises comparing the level of a chitinase-like molecule in the same mammal, or cell or tissue thereof, before and after administration of a compound of interest. A lower level of a chitinase-like molecule expression, production, or activity in the mammal administered the compound when compared to an identical mammal not administered the compound, or to the same mammal prior to administration of the compound, is an indication that the compound is useful for inhibiting a chitinase-like molecule which is therefore a useful potential therapeutic to treat and/or prevent inflammatory disease in a mammal. This is because the present invention discloses, for the first time, that a chitinase-like molecule plays a clear role in the pathology of inflammatory diseases and that inhibiting a chitinase-like molecule treats and/or prevents disease in an art-recognized animal model of inflammatory disease. Clearly, as demonstrated elsewhere herein, a compound that inhibits chitinase-like molecules is an important potential therapeutic compound useful for treatment and prevention of inflammatory disease as demonstrated by the data disclosed herein.

As detailed elsewhere herein, the pathology of many inflammatory diseases is mediated by the expression of IL-13 in an affected cell or tissue. Further, as would be appreciated by the skilled artisan equipped with the present disclosure, the pathology of IL-13 mediated inflammatory diseases is due, in part, to the expression of chitinase-like molecules in an affected cell, organ or system. The methods detailed above include mammals in which the levels of a chitinase-like molecule can be readily assessed using the methods described herein. Thereby, the present invention includes mammals useful for identifying a compound that can be used for the treatment or prevention of inflammatory diseases. More particularly, the invention includes transgenic animals either constitutively or inducible expressing IL-13 in the respiratory tract. Based on the disclosure provided herein, such transgenic mammals, when administered a compound, can be readily assayed for levels of a chitinase-like molecule, whether the assay be for chitinase-like molecule expression or chitinase-like molecule activity. And such methods of identifying a compound useful for treating and/or preventing inflammatory disease relating to using of transgenic non-human mammals to assess whether the compound inhibits a chitinase-like molecule are encompassed in the present invention.

II. Kits

The invention encompasses various kits relating to inhibiting chitinase-like molecules in a mammal which are useful, because, as disclosed elsewhere herein, inhibiting chitinase-like molecules provides a method of treating or preventing inflammatory disease in a mammal. Thus, in one aspect, the invention includes a kit for treating an inflammatory disease in a mammal. The kit comprises an effective amount of a chitinase-like molecule inhibitor. The kit further comprises an applicator and an instructional material for the use thereof to be used in accordance with the teachings provided herein.

The invention includes various kits which comprise a compound, such as a an antibody that specifically binds a chitinase-like molecule, as well as a nucleic acid encoding such an antibody, a nucleic acid complementary to a nucleic acid encoding a chitinase-like molecule but in an antisense orientation with respect to transcription, a ribozyme capable of cleaving a single-stranded chitinase-like molecule RNA, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes kits for treating or preventing an inflammatory disease and an inflammatory disease mediated by IL-13. The kit is used pursuant to the methods disclosed in the invention. Briefly, the kit may be used to contact a mammal with a chemical compound that inhibits chitinase-like molecules, or a nucleic acid complementary to a nucleic acid encoding a chitinase-like molecule where the nucleic acid is in an antisense orientation with respect to transcription to reduce expression of a chitinase-like molecule, or with an antibody that specifically binds with a chitinase-like molecule or a nucleic acid encoding the antibody, wherein the decreased expression, amount, or activity of a chitinase-like molecule mediates an beneficial effect in the mammal. Moreover, the kit comprises an applicator and an instructional material for the use of the kit. These instructions simply embody the examples provided herein.

The kit includes a pharmaceutically-acceptable carrier. The composition is provided in an appropriate amount as set forth elsewhere herein. Further, the route of administration and the frequency of administration are as previously set forth elsewhere herein.

EXPERIMENTAL EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

The materials and methods used in the experiments presented in this Example are now described.

Materials and Methods

Generation of Transgenic Mice: Transgenic mice constitutively expressing lung-tissue specific IL-13 were generated using the CC10-IL-13 construct. The construct comprising the Clara cell 10 kDa protein (CC10) promoter, murine IL-13 cDNA, reverse tetracycline transactivator (rtTA), and human growth hormone intronic and polyadenylation sequences (hGH) was prepared as described in Zhu et al. (1999, J. Clin. Invest. 103:779–788). Standard pronuclear injection was performed as described in Hogan et al. (1986, Manipulating the Mouse Embryo: A Laboratory Manual, Cold Spring Harbor, N.Y.). Resultant mice were screened and founder animals were identified using both Southern blot and PCR. The founder mice were bred onto a C57BL/6 background as described in Zhu et al.(1999, J. Clin. Invest. 103:779–788).

Figure 5:
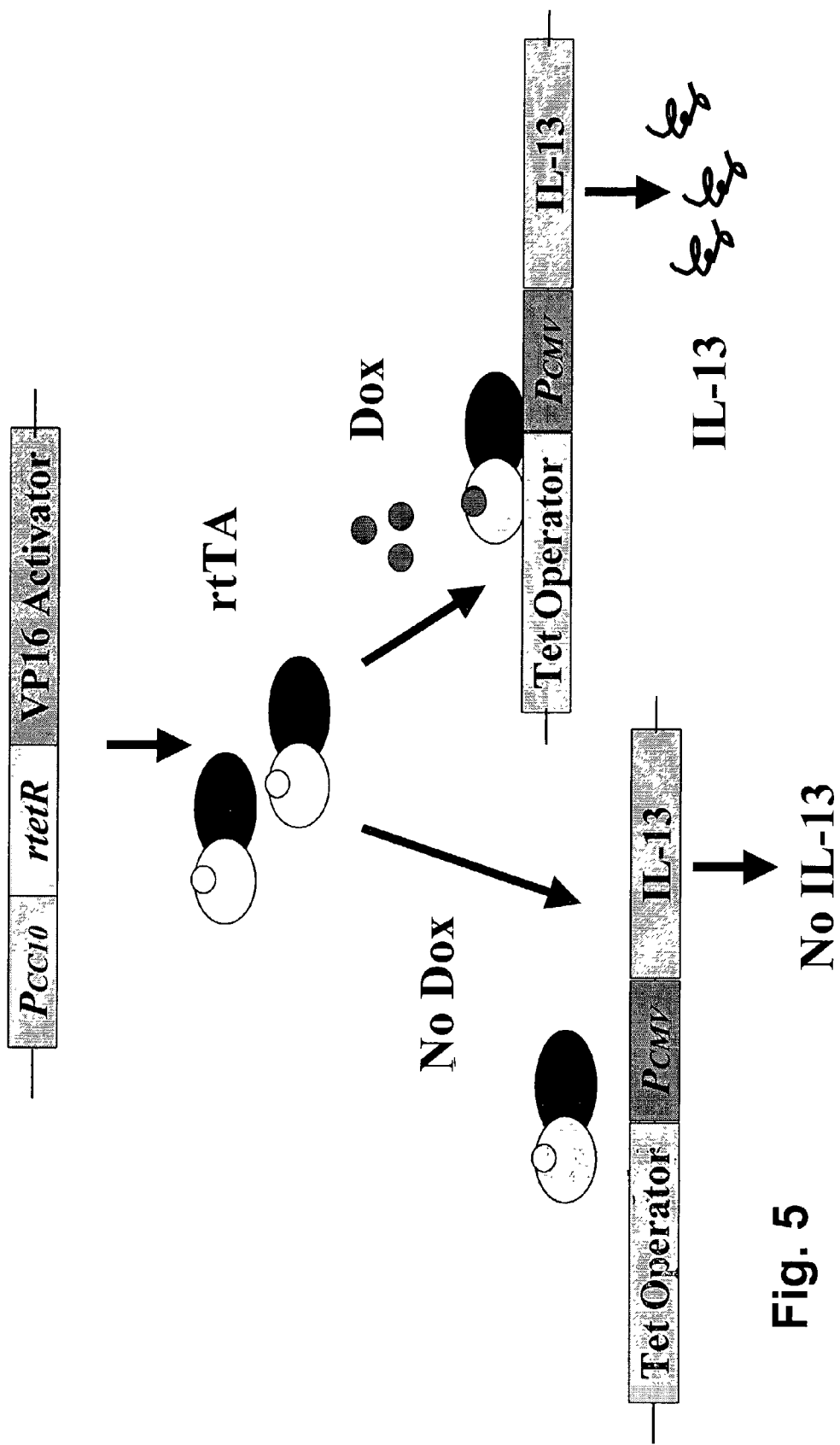
FIG. 5 is a schematic representation of the doxycycline (dox) inducible constructs used to generate the inducible CC10-rtTA-IL-13 transgenic mice.
Figure 8:
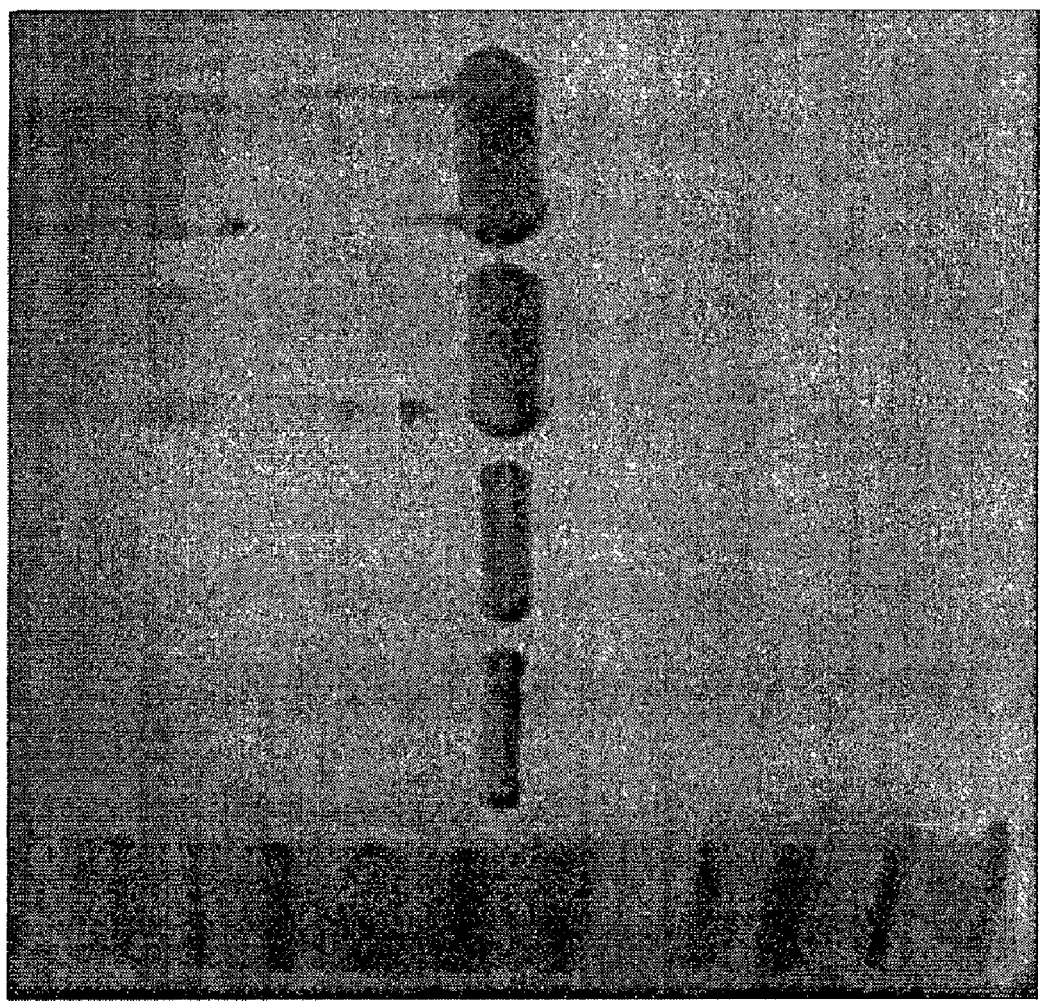
FIG. 8 depicts a Coomassie blue stained SDS-PAGE gel comprising partially purified crystals from bronchioalveolar lavage (BAL) fluid of CC10-IL-13 transgenic mice. The single protein bands had a molecular weight of approximately 45 kDa.

The generation of externally regulatable transgenic mouse system comprised two constructs (FIG. 5). The first construct (CC10-rtTA-hGH), as described in Zheng et al. (2000, J. Clin. Invest. 106:1081–1093), comprised the CC10 promoter, the rtTA transactivator, and the hGH intronic, nuclear localization and polyadenylation sequences. The rtTA fusion protein comprised a mutated tet operator binding protein (tet-OBP) and the herpesvirus VP-16 transactivator (Gossen et al., 1995, Science 268:1766–1769). The second construct (tet-O-CMV-IL-13), comprised a polymeric tetracycline operator (tet-O), minimal cytomegalovirus (CMV) promoter, IL-13 cDNA, and hGH intronic, polyadenylation and nuclear localization signals, was prepared as described in Ray et al. and Zheng et al.(1997, J. Clin. Invest. 100: 2501–2511 and 2000, J. Clin. Invest. 106:1081–1093). Transgenic mice were prepared by simultaneous microinjection of constructs into oocytes, as described in Hogan et al. (1986, Manipulating the Mouse Embryo: A Laboratory Manual, Cold Spring Harbor, N.Y.). Mice were screened by PCR and Southern blot from tail biopsy DNA as described in Zhu et al. and Zheng et al. (1999, J. Clin. Invest., 103:779–788). Four founder mice were then bred with C57BL/6 mice to create transgenic mice with inducible IL-13 expression in the lungs.

Generation and Administration of Anti-AMCase Antibodies

Polyclonal antibodies to AMCase were generated by immunizing rabbits with a peptide derived from AMCase (SEQ ID NO: 18, amino acids 428–446, which are ADKADGLYPVADDRNAFWQ; SEQ ID NO:13) using methods well known in the art and described in, for example, Harlow et al. (1989, Antibodies: A Laboratory Manual, Cold Spring Harbor, N.Y.).

Wild type mice were sensitized to OVA and challenged with OVA on three successive days as described elsewhere herein. Sensitized mice were administered 0.5 ml of anti-AMCase antibodies or control serum intraperitoneally every other day starting the day before the first aerosol exposure.

Histologic Analysis: Mice were sacrificed by cervical dislocation and a median sternotomy was performed. The right heart was perfused with calcium and magnesium free phosphate buffered saline (PBS). The heart and lungs were removed en bloc, and the lungs were fixed to 25 cm pressure with neutral buffered 10% formalin. They were then fixed overnight in 10% formalin, embedded in paraffin, sectioned at 5 µm, and stained. Hematoxylin and eosin (H&E), Mallory's trichrome, periodic acid-Schiff with diastase (D-PAS), alcian blue at pH 2.5, PAS/alcian blue, modified Congo red, and Papanicolau stains were used for histological analysis.

Hydroxyproline Assays

Total lung collagen was determined by analysis of hydroxyproline content. Briefly, lungs were harvested on specified times and homogenized in 2 ml of PBS, pH 7.4, with a Tissue Tearor (PRO-Scientific, Monroe, Conn.). One-half milliliter of each sample (both lungs) was then digested in 1 ml of 6 N HCl for 8 hours at 120° C. Five microliters of citrate/acetate buffer (5% citric acid, 7.24% sodium acetate, 3.4% sodium hydroxide, and 1.2% glacial acetic acid, pH 6.0) and 100 µl of chloramine-T solution (282 mg of chloramine-T, 2 ml of n-propanol, 2 ml of $H_2O$, and 16 ml of citrate/acetate buffer) were added to 5 µl of sample, and the samples were left at room temperature for 20 minutes. Next, 100 µl of Ehrlich's solution (2.5 g of 4-(dimethylamino) benzaldehyde (Aldrich, Milwaukee, Wis.), 9.3 ml of n-propanol, and 3.9 ml of 70% perchloric acid (Eastman Kodak, Rochester, N.Y.) were added to each sample, and the samples were incubated for 15 minutes at 65° C. Samples were cooled for 10 minutes and read at 550 nm on a Beckman DU 640 spectrophotometer (Fullerton, Calif.). Hydroxyproline (Sigma, St. Louis, Mo.) concentrations from 0–10 µg/ml were used to construct a standard curve. (Keane et al. J Immunol. 1999, 163:5686–82.)

Bronchoalveolar Lavage (BAL) and Quantification of IL-13 levels: Mice were killed by cervical dislocation and a median sternotomy was performed. The trachea was isolated by blunt dissection and small caliber tubing was inserted and secured in his airway. Three successive volumes of 0.75 ml of PBS with 0.1% bovine serum albumin (BSA) were instilled and gently aspirated and pooled. Each BAL sample was centrifuged and the supernatants were stored at −70° C. Cell numbers were assessed with hemocytometer and cellular differential counts were undertaken on cytospin preparations. IL-13 levels were determined by ELISA using a commercial kit according to the manufacturer's instructions (R&D Systems, Minneapolis, Minn.).

Physiological Airway Assessment Assays: Age- and gender-matched littermates were evaluated by both invasive and non-invasive physiological assessment techniques.

The non-invasive techniques were used to determine the baseline airways resistance and the level of airways hyper-responsiveness (AHR) in unrestrained, conscious mice. That is, animals were assessed using barometric plethysmography using whole body plethysmography (Buxco Electronics Inc., Troy, N.Y.) as described in Hamelmann et al. (1997, Am. J. Resp. Crit. Care Med. 156:766–775) and Kline et al. (1998, J. Immunol. 160:2555–2559). Briefly, mice were placed into whole body plethysmographs interfaced with computers using different pressure transducers. Tidal volume, respiratory rate, and enhanced pause ($P_{enh}$) measurements were made. Airway resistance is expressed as $P_{enh}=[(T_e/0.3T_r)-1]\times[2\ P_{ef}/3\ P_{if}]$, where $P_{enh}$=enhanced pause, $T_e$=expiratory time in seconds, $T_r$–relaxation time in seconds, $P_{ef}$=peak expiratory flow (ml), and $P_{if}$–peak inspiratory flow (ml/s). Increasing doses of methacholine (Sigma Chemical Company, St. Louis, Mo.) were administered using a nebulizer for 120 seconds, and $P_{enh}$ was determined over the following five minutes.

Invasive physiological assessments were performed in anesthetized (pentobarbital, 90 mg/kg) and tracheostomized (18 gauge angiocatheter) age- and sex-matched mice. The changes in the lung volume of the mice were measured plethysmographically by determining the pressure in a Plexiglass chamber using an inline microswitch pressure transducer. Flow was measured by the difference between the volume signal and the transpulmonary pressure as determined by a second microswitch pressure transducer placed in line with the plethysmograph and animal ventilator. Resistance (with resistance due to the tracheostomy catheter eliminated) was measured using the method of Amdur and Mead (1958, Am. J. Physiol. 192:364–368). Baseline measurements of pulmonary resistance were obtained by ventilating the mouse at a volume 0.4 ml and a rate of 150 breaths per minute. Increasing concentrations of methacholine in PBS were administered by nebulization (20 one-ml breaths) using a Devilbiss Aerosonic nebulizer (Model 5000, Devilbiss Health Care, Somerset, Pa.) that produces particles of about 1–3 µm in diameter. Pulmonary resistance was calculated precisely 1 minute later. Stepwise increases in methacholine dose were then administered until the pulmonary resistance, in comparison with the baseline level, had at least doubled. All animals received serial threefold increases in methacholine from 1 to 100 mg/ml. The data are expressed as the $PC_{100}$ (provocative challenge 100), which is the dose at which pulmonary resistance was 100% above the baseline level as calculated by linear regression analysis.

Lung Volume Assessment: Lung volume assessment was performed exactly as described in Zheng et al. (2000, J. Clin. Invest. 106:1081–1093)

Doxycycline Administration: All inducible transgenic mice were maintained on normal water until transgene activation was desired. Doxycycline (dox) was administered in drinking water (0.5 mg/ml). Dox containing water bottles were wrapped in aluminum foil to prevent light-induced dox breakdown.

mRNA Analysis: mRNA levels were assessed using Northern blot and reverse-transcriptase polymerase chain reaction (RT-PCR). Total cellular RNA was extracted from mouse tissue using TRIZOL™ (Invitrogen, Carlsbad, Calif.) per the manufacturer's instructions. Primers specific for YM (YM-1 forward primer: TGGAATTGGTGCCCCTACAA; SEQ ID NO:1, YM-1 reverse primer: AACTTGC ACTGTGTATATTG; SEQ ID NO:2, YM-2 forward primer: AACCTCAGACAT TCATTA; SEQ ID NO:3, YM-2 reverse primer: TGGTCCTTCCAGTAGGTAATA; SEQ ID NO:4, YM-3 forward primer: TATAAATCTCCATTTGACAC; SEQ ID NO:5, YM-3 reverse primer: CCTAATTTATTGTCCTTGAC; SEQ ID NO:6) and AMCase (AMCase forward primer: ATCTGCAGTGGACACACCTTCATCCTGA; SEQ ID NO: 7, AMCase reverse primer: ATGAATTCAACAAGCCCTGCTTGACAAT; SEQ ID NO:8) were used in RT-PCR to amplify and detect these transcripts. Reverse transcription and PCR were performed using the Access RT-PCR kit from Promega (Madison, Wis.) per the manufacturer's instructions.

In Situ Hybridization of Murine Lungs: In situ hybridization was used to localize expression of both YM and AMCase in transgenic animals. Lung tissues were fixed in formaldehyde and processed into paraffin. Five micron sections were cut, deparaffinized, and treated with proteinase K (20 µg/ml, 37° C., 20 min). Tissues were then treated with 0.1 M triethylnolamine/0.25% acetic anhydride (pH 8) for 10 min at room temperature and rinsed in PBS. Antisense and sense probes for YM (YM antisense probe: TCCTCGAGACCCAGGGTACTGC; SEQ ID NO:9, YM sense probe: TATCTAGAGGATCTTCCTACCAGC; SEQ ID NO:10) and AMCase (AMCase antisense probe: TCGCTCGAGAACAAGCCCTGCTTGACAAT; SEQ ID NO:11, AMCase sense probe: GCTCTAGATGGACACACCTTCATCCTGA; SEQ ID NO:12 were generated by cloning a fragment of mouse AMCase cDNA or YM cDNA into vector pBS II KS with T3 and T7 primer sequences flanking the multiple cloning sites (Stratagene, La Jolla, Calif.). The oligonucleotide primers with XbaI and XhoI restriction enzyme sites incorporated, were used to amplify DNA fragments from total lung RNA of an IL-13 transgene (+) mouse. The RT-PCR products were digested with XbaI and XhoI and cloned into the vector pBS II KS. Sense and antisense RNA probes were generated, labeled with a digoxigenin RNA labeling kit (Roche, Indianapolis, Ind.), denatured at 65° C., and added to commercially available hybridization buffer (Ambion, Austin, Tex.) at 6 ng/µl, and the hybridization mixture was incubated with tissue overnight at 52° C. The tissues were then washed twice with 4×SSC for 5 min at room temperature, twice with 2×SSC for 10 min at 37° C., and incubated with RNase A (10 µg/ml) for 45 min at 37° C. This was followed by two 10-min washes in 2×SSC at room temperature and three 20-min washes in 0.2×SSC at 50° C. Probes were detected by overnight incubation with sheep antibodies (Abs) to digoxigenin labeled with alkaline phosphatase (Roche) followed by 4-nitroblue tetrazolium chloride/5-bromo-4-chloro-3-indoylphosphate, as described by the manufacturer.

Crystal Purification and Analysis: Crystals were purified using a ficoll-gradient washing procedure as described by Guo et al. (2000, J. Biol. Chem. 275:8032–8037). Briefly, BAL fluid from IL-13 transgenic mice was loaded, in a ratio of 1:5, on top of Histopaque-1119 with a density of 1.119 grams/ml (Sigma, St. Louis, Mo.) and centrifuged at 250×g for 10 minutes at 4° C. The supernatant was removed and the pellet was resuspended in PBS and centrifuged twice more as above. The resulting pellet was dissolved in SDS-PAGE sample buffer and boiled for 10 minutes before electrophoresis. SDS-polyacrylamide gel electrophoresis was performed under reducing conditions using Tris-glycine 4–20% gradient gels (BioRad, Hercules, Calif.). Protein bands were visualized by staining with Commassie Blue, excised with a scalpel and subjected to in-gel tryptic digestion before mass spectrometric analysis. The Coomassie Blue stained protein band around 40 kDa was excised and washed with 50 mM ammonium bicarbonate, 50% acetonitrile for 30 minutes, followed by a 10 mM ammonium bicarbonate, 50% acetonitrile wash for an additional 30 minutes. After washing, the gel pieces were dried and re-hydrated with 0.1 µg modified trypsin (Promega, Madison, Wis.) in 15 µl 10 mM ammonium bicarbonate. Digestion was done at 37° C. for 24 hours. Matrix assisted laser desorption ionization mass spectrometry (MALDI-MS) was carried out on 1.0 µl (<5%) of the digest using a Micromass TofSpec SE mass spectrometer (Micromass, Beverly, Mass.) in reflectron mode. Prior to MALDI-MS the sample was mixed with 1.0 µl of alpha-cyano-4-hydroxy cinnamic acid matrix solution (4.5 mg/ml in 0.05% trifluroacetic acid, 50% acetonitrile) plus 1 µl of internal calibrants and then spotted onto a new single use target. The samples were then allowed to air dry at room temperature. The internal calibrants used were 50 femtomoles bradykinin (monoisotopic M+H is 1060.57) and 125 fmols ACTH Clip 18–39 (monoisotopic M+H is 2465.20). A total of 92 peptide masses (monoisotopic) were submitted for peptide mass database searching using Peptide Search (non-redundant database at the EMBL) and ProFound (at Rockefeller University for non-redundant database at NCBI). By using either algorithm, 24 of the 92 peptide masses matched mouse chitinase 3-like 3 protein (also called YM-1 and ECFL-precursor) with a minimum coverage of 59%. A subsequent search using unmatched peptide masses of the first pass did not yield any meaningful matches.

Chitinase Activity Assays: BAL fluid, collected as previously described, was used in a chitinase activity assay. The chitinase activity in BAL was assessed using a fluorescence assay. Fluorogenic 4-methylumbelliferyl β-D-N,N'-diacetylchitobioside was used as a substrate. Assays were performed as the following. BAL samples were incubated with the substrate at a concentration of 0.02 M in citrate/phosphate buffer (0.1 M/0.2 M), pH 5.2. After 15 min at 37° C., the reaction was stopped by adding 1 ml of 0.3 M glycine/NaOH buffer, pH 10.6 and the fluorescent 4-methylumbelliferone was determined with a fluorimeter at excitation of 350 nm and emission 450 nm. A standard curve was generated using 4-methylumbelliferone (Sigma). Chitinase extract from Serratia marcescens was used as a positive control (Sigma).

Aeroallergen Ovalbumin (OVA) Sensitization and Challenge Tests: OVA sensitization and challenge were accomplished using modifications of the protocols previously described by Yang et al. (1998, J. Exp. Med. 188:1739–1750). Briefly, wild type mice received intraperitoneal (i.p.) injections containing 20 µg of avian OVA (Sigma) complexed to alum (Resorptar; Indergen, New York, N.Y.). This process was repeated 5 days later. After an additional 7 days, animals received aerosol challenge with OVA (1% w/v) in endotoxin-free PBS or the animals received endotoxin-free PBS alone. The aerosol challenge was accomplished in a closed 27×20×10 cm plastic aerosol chamber in which the mouse was placed for 40 minutes. The aerosol was generated using an Omron NE-U07 ultrasonic nebulizer (Omron Healthcare, Vernon Hills, Ill.). Mice were sacrificed twenty-four hours, forty-eight hours, and seven days after OVA challenge.

Relative Induction of YM and AMCase: Affymetrix murine GENE CHIP arrays (Santa Clara, Calif.) comprising 12,200 oligonucleotides were used to analyze IL-13 induced gene expression in the murine lung. The levels of gene expression in IL-13 expressing, dox-inducible and control mice were analyzed. The expression levels were standardized using housekeeping genes (e.g., actin, GAPDH, hexokinase and the like), and a stimulation index was calculated by dividing the target ratio in transgene (+) animals by the target ratio in transgene (−) animals. Similar gene expression studies were performed in mice constitutively expressing IL-13 and controls. GENE CHIP assays were performed as follows. Total RNA was isolated from the lungs of IL-13 transgenic mice and littermate negative controls with Trizol reagent (Life Technologies, Gaithersburg, Md.). To prepare samples for Affymetrix GENECHIP analysis, cDNA was generated from 15 µg of total RNA by use of a modified oligo-dT primer and a 5' T7 RNA polymerase promoter oligo primer with the Superscript Choice System for cDNA Synthesis (Life Technologies). After phenol-chloroform extraction and ethanol precipitation, one-half of the cDNA reaction (0.5–1.0 µg) was used as a template for an in vitro transcription reaction with biotinylated UTP and CTP (BioArray High Yield kit, Enzo Biochem, Farmingdale, N.Y.) by following the manufacturer's protocol. The resulting cRNA was purified on an affinity resin column (RNeasy, Qiagen, Valencia, Calif.) and quantified by ultraviolet (UV) absorbance. For each reaction, 15 µg of biotinylated cRNA were randomly fragmented to an average size of 50 nucleotides by incubating them at 94° C. for 35 min in 40 mM Tris-acetate, pH 8.1, 1,000 mM potassium acetate, and 30 mM magnesium acetate. The fragmented cRNA was divided into two aliquots that were each used for hybridization to an Mu11K Affymetrix GENECHIP according to the manufacturer's protocol (Affymetrix, Santa Clara, Calif.), with a duplicate data set generated for all samples. Each target array was washed and scanned (Hewlett-Packard, GeneArray Scanner G2500A). Data were analyzed with the Affymetrix GENECHIP software algorithm to generate "average difference" and/or degree of difference after the values were normalized. The values obtained from wild type C57BL/6 littermate controls were used as baseline and the values from IL-13 transgenic mice were expressed as relative fold-increases.

Ribonuclease Protection Assay: Ribonuclease protection assays were performed using the mCK-1 template kit (PharMingen San Diego, Calif.). Ribonuclease protection assays were performed as described in, for example, Sambrook et al. (1989, Molecular Cloning: A Laboratory Manual, Cold Spring Harbor Laboratory, New York) and Ausubel et al., 1997 (Current Protocols in Molecular Biology, John Wiley & Sons, New York).

Allosamidin Administration: Allosamidin (Eli Lilly and Co., Greenfield, Ind. and Industrial Research Limited, Lower Hutt, New Zealand) was administered to inducible IL-13 overexpressing mice and OVA exposed wild type mice. Mice were given 0.1 mg/kg to 10 mg/kg allosamidin i.p. or vehicle control (PBS). The animals were then sacrificed and BAL fluid analysis, histologic and morphometric analysis, and lung volume assessment were performed as described elsewhere herein.

The results of the experiments presented in this Example are now described.

Transgenic Mice Constitutively Expressing IL-13: Transgene (+) mice expressing IL-13 constitutively exhibited high levels of IL-13 in BAL fluid (up to 2.1 ng/ml) and detectable IL-13 mRNA in the lungs. IL-13 mRNA could not be detected in the skin and other visceral organs of the transgenic mice, indicating lung-specific expression of IL-13. Trangene (−) mice did not demonstrate detectable levels of IL-13 or IL-13 mRNA in BAL fluid or in the lungs.

Figures 2A, 2B:
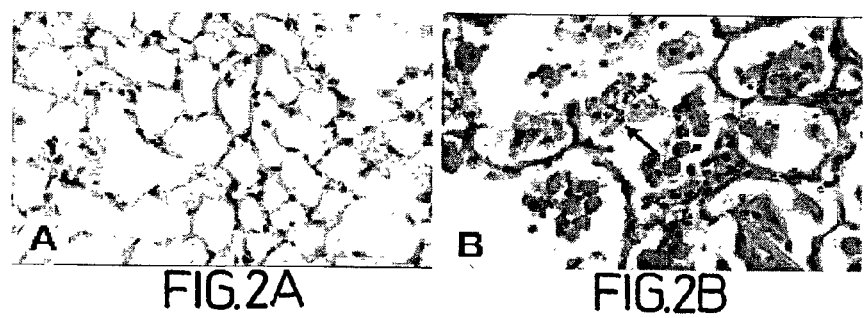
FIG. 2A through FIG. 2D, is an image depicting hematoxylin and eosin (H&E) stained lung tissues from control normal and CC10-IL13 (constitutively expressing IL-13) mice.
Figures 2C, 2D:
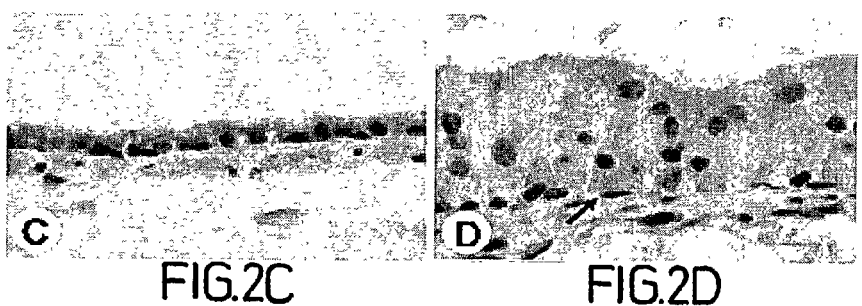

Histologic analysis of transgene (+) mice demonstrated multiple asthma-like features. These features include eosinophil, lymphocyte, and macrophage-rich inflammatory responses around the small and large airways and in the adjoining parenchyma. This response was milder in young animals, or animals with low levels of BAL IL-13, and more prominent in older animals or those with higher BAL levels of IL-13. Epithelial hypertrophy was evident in the conducting and small airways as well (FIG. 2).

Constitutive expression of lung-specific IL-13 also resulted in COPD-like alveolar enlargement and wall rupture, as well as focal organization of crystalline material into Masson body-like fibrotic foci. Further, long, thin, needle-like crystals were seen in the macrophages, alveoli, and occasionally, the airways of transgene (+) animals.

Figure 3A:
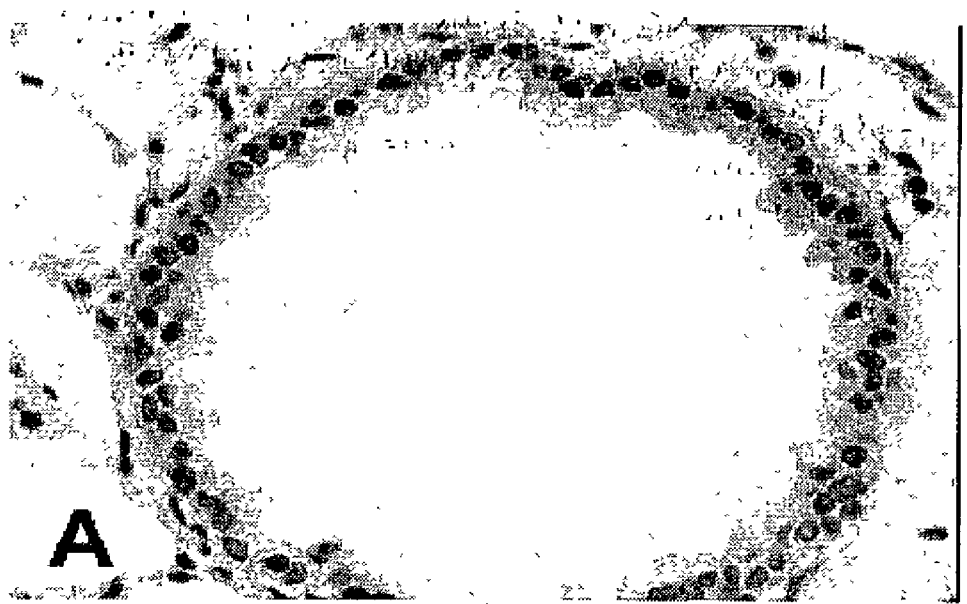
FIG. 3A and FIG. 3B, is an image depicting periodic acid-Schiff with diastase (D-PAS) staining of airways from control and CC10-IL-13 mice.
Figure 3B:
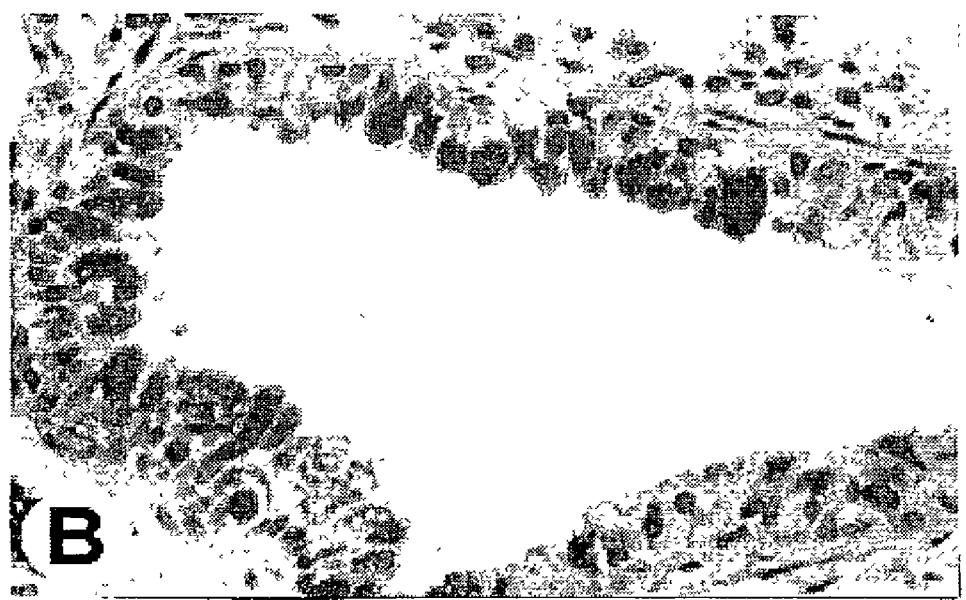

As mucus metaplasia and enhanced mucin gene expression are characteristic of both asthma and COPD, the effect of constitutive IL-13 expression on airway mucus was undertaken. Both PAS and alcian blue staining demonstrated that mucus accumulation was prominent in the airways of transgene (+) mice, but not in transgene (−) littermates (FIG. 3). Impressive increases in the mucin genes MUC5AC, MUC2 and MUC4 mRNA were also evident in transgene (+) mice.

Airway remodeling with subepithelial fibrosis is a well documented feature of the asthmatic airway, and disordered repair and parenchymal fibrosis are often noted as aspects of emphysema. These features of inflammatory diseases are associated with increased collagen deposition. Accordingly, Masson's trichrome stains, sirius red, and hydroxyproline assays were used to evaluate the collagen deposition in the airways of transgene (+) and (−) animals.

Figure 4A:
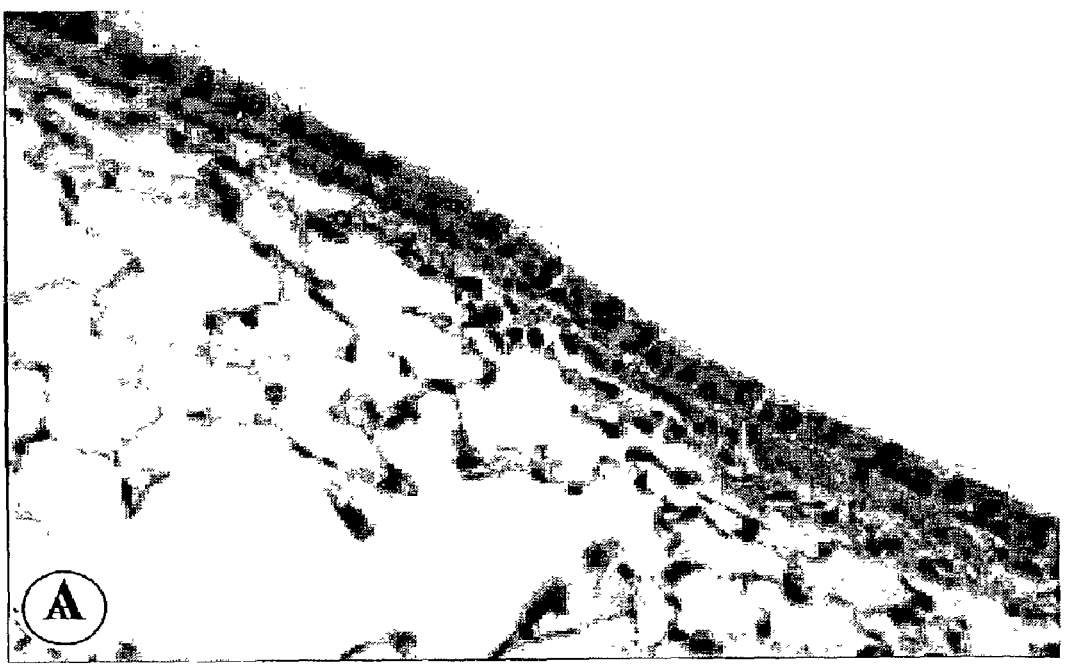
FIG. 4A and FIG. 4B, depicts trichrome staining of airways in CC10-IL-13 mice.
Figure 4B:

A small amount of collagen was seen in and near the airway wall in transgene (−) animals, and loosely packed collagen was detected in the bronchovascular bundles. In sharp contrast, enhanced collagen deposition was seen in the subepithelial region and aventitia of the small and large airways of transgene (+) animals (FIG. 4), similar to findings in human airway disorders. Scarring and parenchymal fibrosis was observed in older animals, and these features increased with age. Increased levels of hydroxyproline could be detected as early as 4–6 weeks after IL-13 production, and three month old animals had significantly (4.1 fold, $p<0.001$) higher hydroxyproline levels than transgene (−) animals.

Both asthma and COPD patients demonstrate airway obstruction and AHR (an exaggerated bronchospastic response to non-specific agonists like methacholine). Accordingly, studies were undertaken to determine if these airway alterations were present in the IL-13 transgenic animal model. Baseline airway resistance was mildly elevated in transgene (+) animals. In addition, AHR was also seen after methacholine challenge, as determined using invasive and non-invasive assessment methodologies. These data indicate asthma- and COPD-like physiological alterations are present in the IL-13 transgenic model.

Inducible Transgenic Mice: The lung-specific inducible transgenic animal system allows for temporal control of IL-13 expression in the murine lungs. This mimics the waxing and waning patterns of IL-13 expression seen in asthma and COPD and circumvents the abnormalities caused by the in utero or neonatal gene expression seen with other transgenic models.

Inducible transgenic mice were kept on normal (dox-free) water until one month of age. IL-13 was not detected in the BAL fluid from transgene (−) animals on dox or normal water. In the absence of dox, levels of BAL IL-13 $\leq$ 75 pg/ml were found in transgene (+) animals. Within 24 hours of dox administration, transgene (+) animals demonstrated increased BAL IL-13 levels, and steady state levels ranging from about 0.5 to 1.5 ng/ml were observed within 96 hours after dox administration. BAL IL-13 levels returned to background levels within 96 hours after dox administration ceased. IL-13 mRNA was only detectable in pulmonary tissues of transgene (+) animals.

H&E and trichrome staining demonstrated that lungs obtained from transgene (−) mice given normal water or dox-containing water did not demonstrate any histological abnormalities, nor could those lungs be distinguished from the lungs obtained from transgene (+) mice given normal water. However, transgene (+) mice given normal water did show mild mucus metaplasia after D-PAS staining.

Conversely, transgene (+) mice given dox water exhibited notable inflammatory, mucus, and structural alterations. As little as seven days after dox administration, inflammation in BAL fluid was prominent. At this time point, there was a 7.5 fold increase in cell recovery from BAL fluid and a significant increase in the percentage of BAL fluid eosinophils (63%, $p<0.001$) in transgene (+) mice given dox water. Lymphocyte and macrophage recovery were also significantly increased ($p<0.01$) in these mice. Also, mononuclear, lymphocytic and eosinophilic infiltrates were prominent in airway and peribroncheal structures, as was an increase in mucus metaplasia. Additionally, substantial increases in MUC-5AC, MUC-2, and MUC-4 mRNA were noted. Chronic administration of dox resulted in subepithelial fibrosis, alveolar enlargement, and crystal deposition, very similar to that observed in transgenic mice constitutively expressing IL-13.

The emphysema in COPD is defined pathologically as the abnormal enlargement of the airspaces distal to the terminal bronchial of the lung (Senior and Shapiro, 1998, Fishman's Pulmonary Diseases and Disorders, Vol. 1, McGraw-Hill, N.Y.). As previously noted, mice expressing IL-13 constitutively displayed enlarged alveoli. To determine whether this enlargement was due to faulty development or to the destruction of lung tissue in a normally formed lung, inducible transgenic (+) mice were given dox water only after full lung development was completed. After dox administration, IL-13 induced alveolar enlargement was apparent using both histologic and morphometric techniques. In the absence of dox, normal alveoli were seen in both transgene (−) and (+) animals (FIG. 6).

YM Crystal Deposition in IL-13 Overexpressing Mice: As previously noted, crystals were seen in both inducible and constitutive IL-13 transgene mice. The presence of the crystals was both dose- and time-dependent. In constitutive IL-13 mice, crystals could be seen at the earliest time point assessed (1 month), and impressive crystal accumulation was evident in three month old animals. Similarly, the inducible IL-13 mice displayed crystals in various tissues and cells of the airway at about the same time intervals after dox administration. In young mice, crystals were most commonly seen in macrophages, parenchyma and alveoli, and less commonly in distal airways. In older animals, considerable alveolar and parenchymal crystal deposition was noted, including many alveoli completely filled with crystalline deposits Crystals were multi-faceted, often needle shaped, and approximately 20–120 µm in length (FIG. 7).

Crystals were purified from BAL fluid from constitutive IL-13 transgenic (+) mice using a ficoll density gradient method as described elsewhere herein. These crystals were assayed and determined to be comprised of YM proteins. No other peptides were found in the sample, and YM proteins were not detected in transgene (−) animals, indicating that the crystals in IL-13 transgene (+) animals comprise YM proteins.

Figure 9:
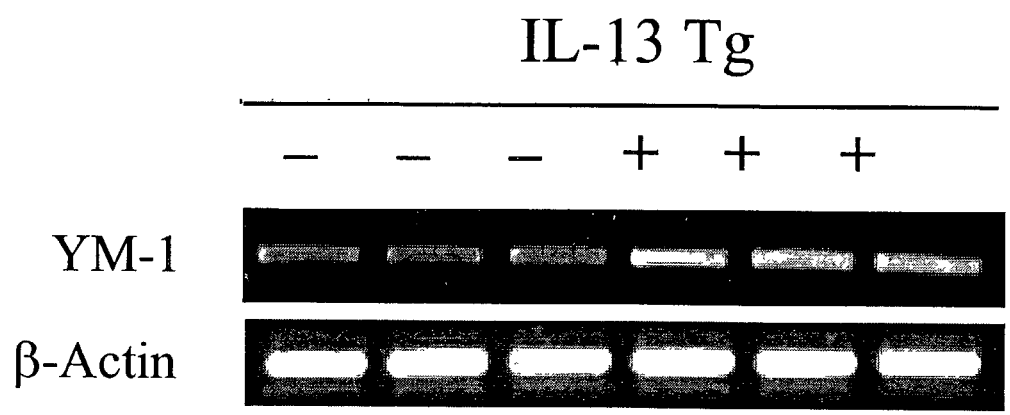
FIG. 9 depicts YM mRNA levels in the lungs of two month old transgene (+) and (−) CC10-IL-13 mice as determined by reverse transcriptase polymerase chain reaction (RT-PCR).
Figure 10A:
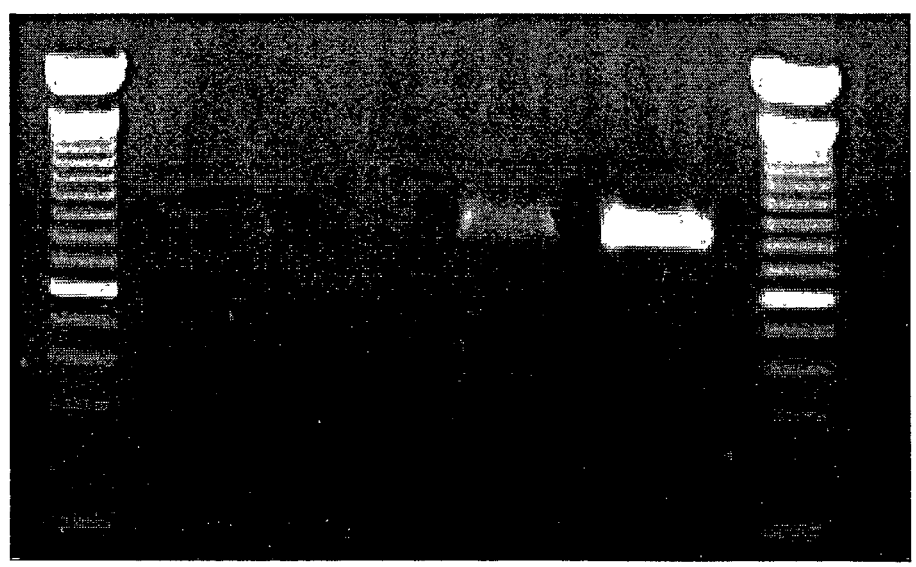
FIGS. 10A and 10B, depicts YM mRNA levels in transgene (−) and (+) CC10-rtTA-IL-13 mice that were randomized to normal or dox water starting at one month of age.
Figure 10B:
Figure 11F:
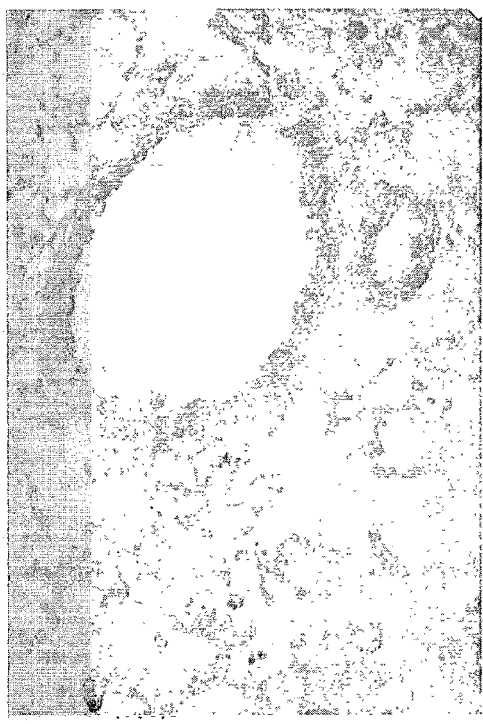
Figure 11H:
Figure 11E:
Figure 11G:
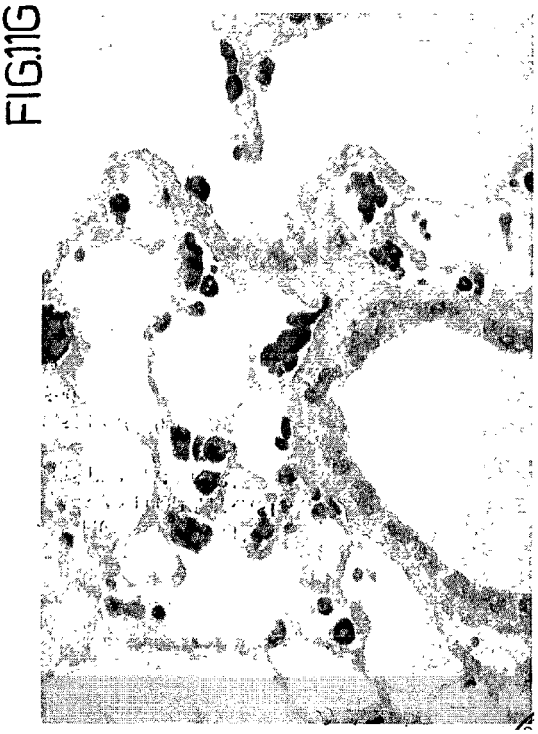

YM Gene Expression in IL-13 Overexpressing Mice: RT-PCR was performed as described herein to determine if YM protein expression was induced by IL-13. In whole lung RNA from transgene (−) animals, YM mRNA was at or near the lower sensitivity limits of the assay (FIG. 9). In stark contrast, in transgenic mice constitutively expressing IL-13, YM mRNA was detected in all time points assessed (1 to 3 month old mice). Inducible transgene (+) mice that did not receive dox demonstrated low levels of YM mRNA, indicating a mildly "leaky" system. Upon administration of dox, striking increases in YM mRNA were observed as little as 48 hours after dox introduction, and high levels of YM mRNA expression continued throughout the three month period in which dox was administered (FIG. 10).

In situ hybridization was used to localize the sites of YM protein production in IL-13 transgenic animals. YM mRNA could not be detected in transgene (−) mice, but impressive levels were detected in transgene (+) animals using antisense probes. In transgene (+) animals, YM localized intensely to macrophages and to airway epithelial cells. It should be noted that YM staining was not detected when the same tissues were probed using sense oligonucleotides (FIG. 11), confirming the specificity of these results.

To ascertain whether cytokine induction of YM mRNA expression was IL-13 specific, RT-PCR analysis was undertaken using whole lung RNA from a variety of other transgenic mice. IL-4 transgenic mice expressed exaggerated levels of YM in their lungs, similar to IL-13 transgenic mice. This coincides with evidence indicating that IL-4 is another important cytokine in human airway disorders, as stated previously elsewhere herein. Transgenic mice constitutively expressing IL-6, IL-11, vascular endothelial growth factor$_{165}$ (VEGF) and IL-10 demonstrated YM mRNA levels comparable to that of IL-13 transgene (−) littermate controls, further confirming that the cytokines postulated to play a role in Th2 dominated respiratory inflammation, i.e., IL-13 and IL-4, are also potent and specific inducers of YM expression.

Figure 12:
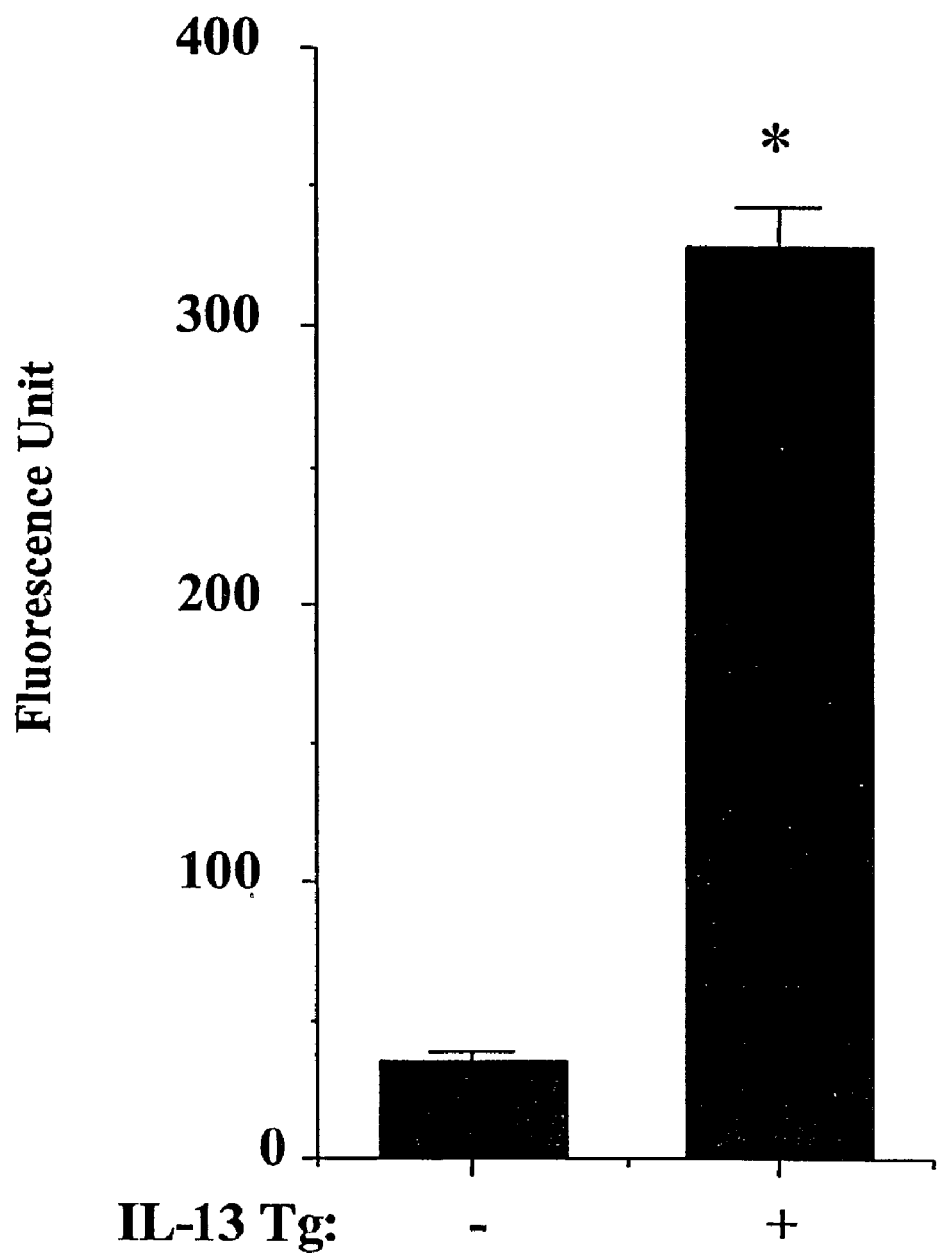
FIG. 12 is a graph depicting chitinase activity in BAL fluids obtained from 2 month old transgene (−) and transgene (+) CC10-IL-13 animals. ($p<0.05$ versus transgene (−))
Figure 14B:
FIG. 14A through 14D, depicts localization of AMCase expression in CC10-IL-13 mice using in situ hybridization.
Figure 14D:
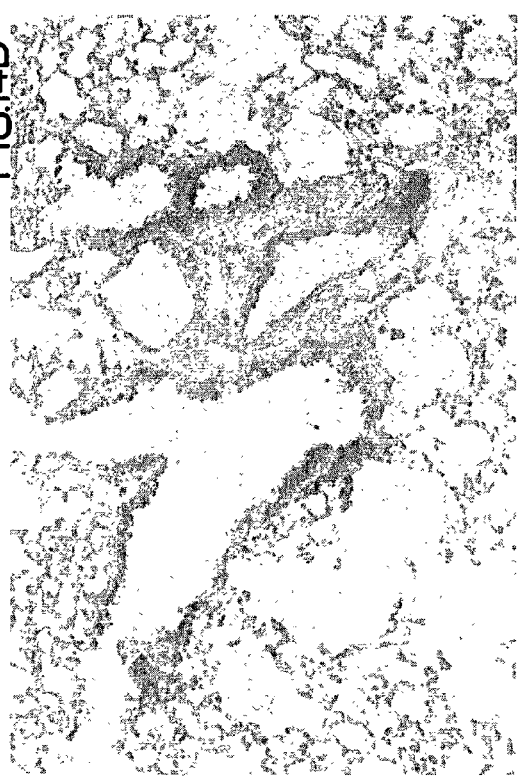
Figure 14A:
Figure 14C:

Chitinase Activity in BAL Fluid from IL-13 Overexpressing Mice: Chitinase activity in BAL fluids from transgene (+) and (−) mice constitutively expressing IL-13 was assayed using methods described elsewhere herein. BAL fluid obtained from transgene (−) mice had levels of chitinase activity $\leq 75$ units/ml. In contrast, an impressive increase in chitinase activity in transgene (+) mice was detected (FIG. 12). That is, chitinase activity was detected in 1 month old transgene (+) animals, and continued to increase as the animals aged. Similarly, chitinase activity was detected in inducible transgene (+) animals as little as two days after dox administration, and this activity also increased over time. Transgenic mice overexpressing IL-4 also demonstrated increased levels of chitinase activity. However, BAL fluid from IL-6, IL-11, VEGF, and IL-10 transgene (+) animals had basal levels of chitinase activity. These data indicate that increased chitinase activity correlates with increased IL-13 and/or IL-4 expression and with increased YM protein expression and crystal deposition in lung tissues.

AMCase Expression in IL-13 Transgenic Mice: Conflicting reports have indicated that YM may or may not have chitinase activity. For instance, both purified and recombinant YM have failed to demonstrate chitinase activity in a number of assays, indicating that it is not a chitinase, but rather a chitinase-like molecule (Chang et al., 2001, J. Biol. Chem. 276:17497–17506). BAL fluid from IL-13 transgene (+) mice demonstrates detectable chitinase activity, indicating that a chitinase family protein may be present in the BAL fluid of these mice. To date, AMCase is the only enzyme identified in murine systems that demonstrates true chitinase activity. To determine whether AMCase expression was augmented in the IL-13 transgene (+) mouse lung, RT-PCR primers specific for AMCase were used, as described above. mRNA levels in transgene (−) littermate controls were near or below detection levels in the assay employed. Conversely, impressive increases in AMCase mRNA levels were found in both constitutive and inducible IL-13 transgenic models. In the former it was noted in animals that were one month to three months of age. In the latter as little as seven days after dox administration, respectively. Similar to YM protein expression, AMCase expression was specific to IL-13 transgenic animals, as it was not detected in lungs from the other transgenic animals (IL-10, VEGF, IL-6, and IL-11) assessed herein.

In situ hybridization was employed to localize AMCase production in IL-13 transgenic mice. Prominent accumulation of AMCase mRNA was detected in epithelial cells and, to a lesser extent, in the macrophages. In contrast, AMCase mRNA was not detected in transgene (−) mice (FIG. 14).

Figure 15A:
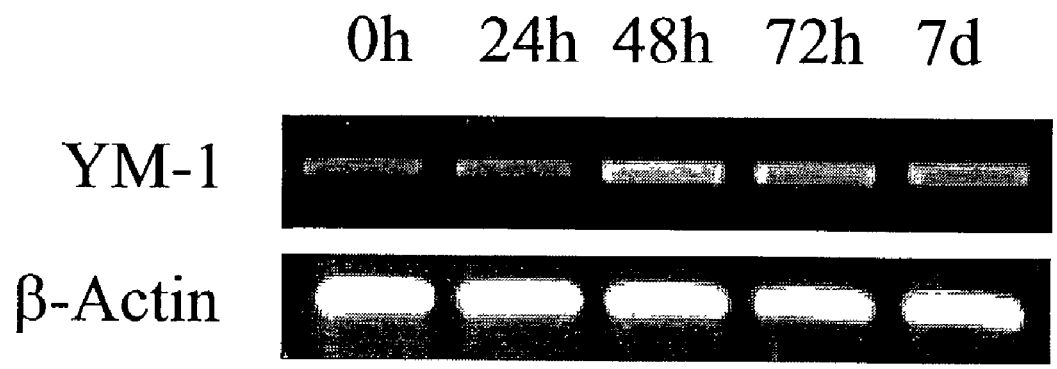
FIG. 15A through FIG. 15C, depicts YM and AMCase mRNA expression and chitinase activity in ovalbumin (OVA) sensitized and challenged wild-type mice, as determined using RT-PCR and chitinase activity assays, respectively.
Figure 15B:
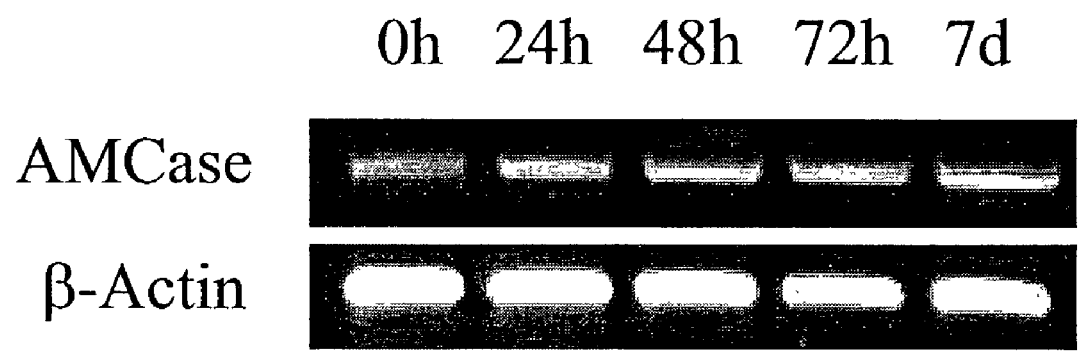
Figure 15C:
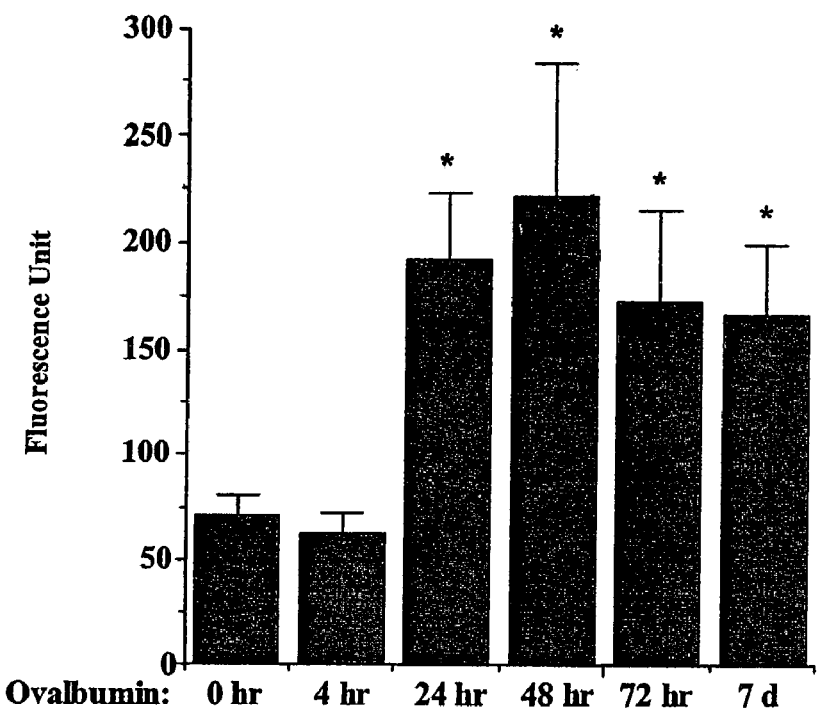
Figure 16A:
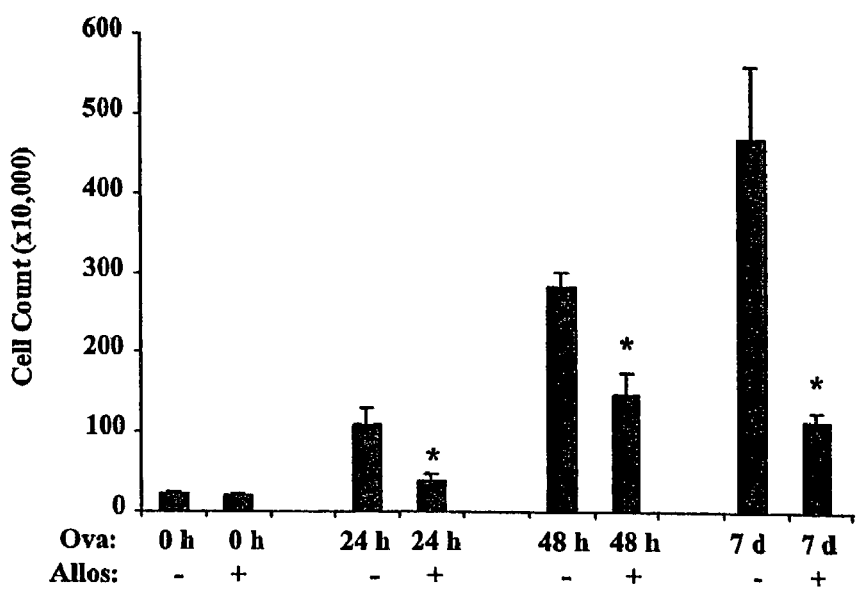
Figure 16B:
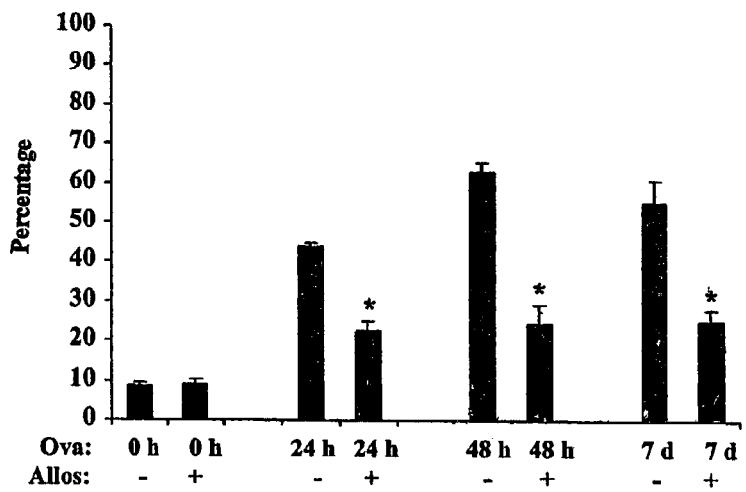
Figure 16C:
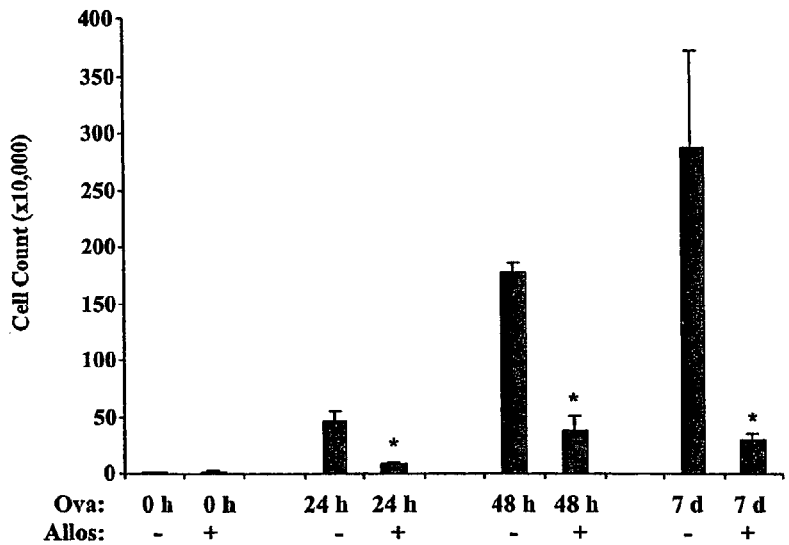
Figure 16D:
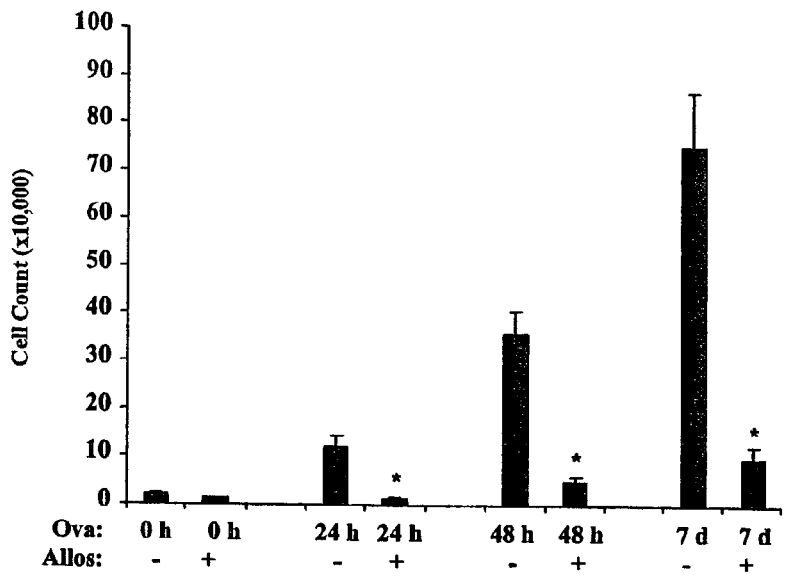
Figure 16F:
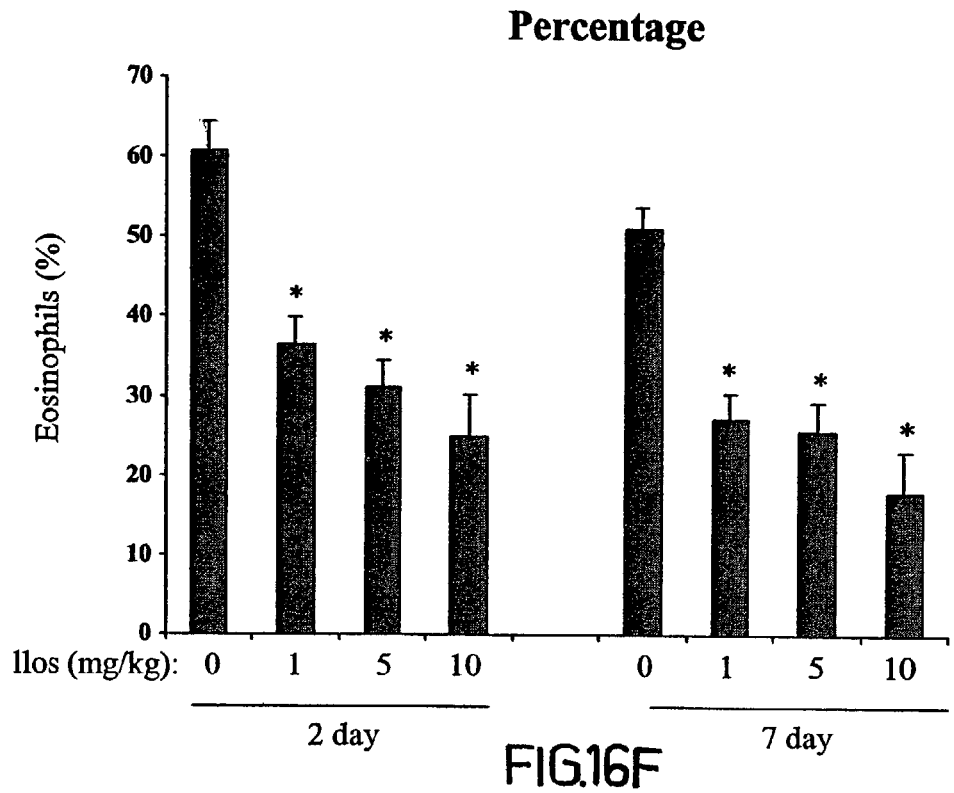
Figure 16G:
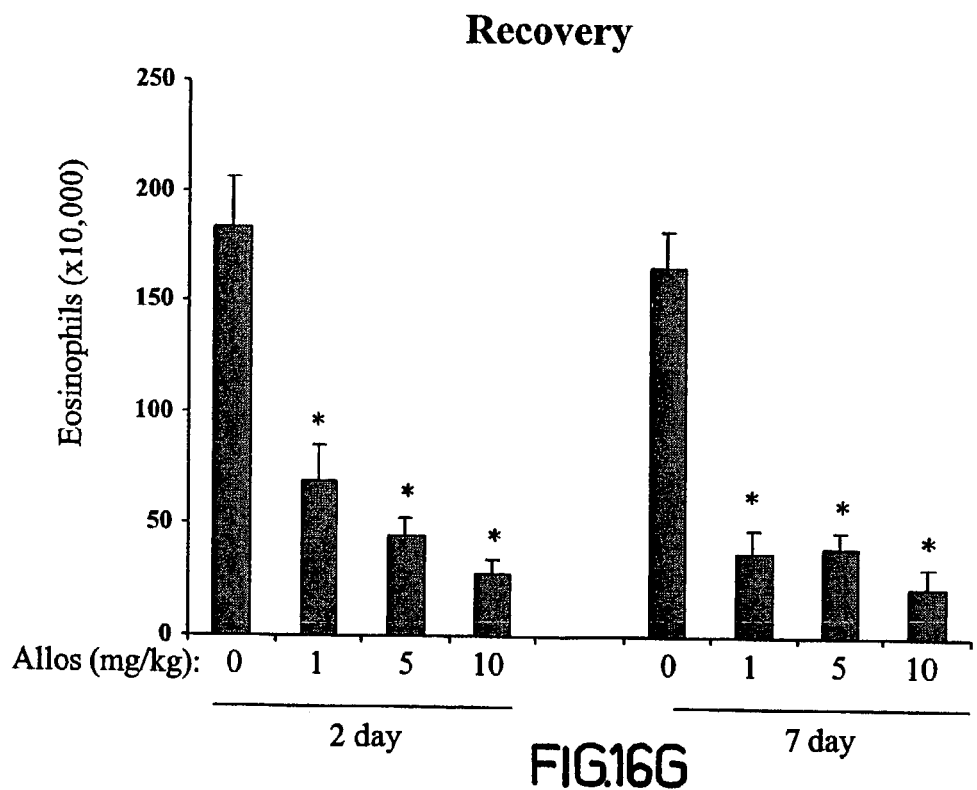
Figure 17:
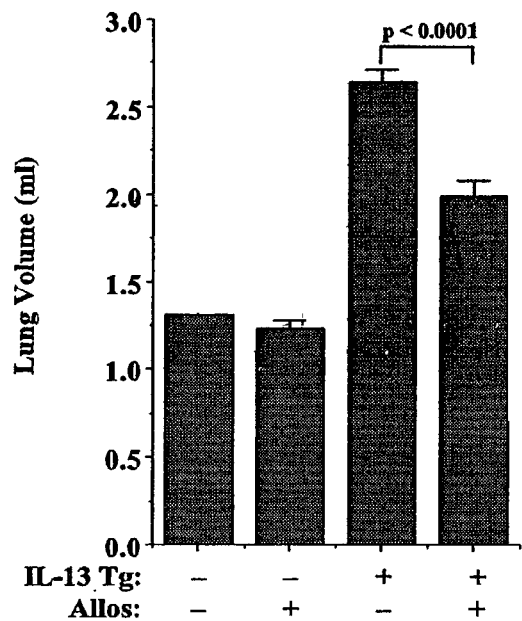
FIG. 17, comprising

Chitinase Gene Expression in an OVA-Induced Murine Asthma Model:

Studies were performed to ascertain whether YM proteins and/or AMCase were induced in the standard Th2-driven murine asthma model. To this end, the chitinase activity of BAL fluid and the expression of these two genes in lungs of OVA sensitized wild type mice was investigated. In animals that were OVA sensitized, but did not receive an OVA challenge, mRNA levels and BAL fluid chitinase activity were near the limits of detection levels of the assays. However, after OVA challenge, YM and AMCase mRNA levels were readily detected and persisted for 7 days after antigen challenge. BAL fluid chitinase activity increased accordingly as well (FIG. 15).

Relative Induction of YM and AMCase: Affymetrix GENE CHIPS, comprising 12,200 oligonucleotides, were used to assess the IL-13 induced gene expression alterations in inducible transgenic animals that had been given dox from 1 month to 2 moths of age, and compared with transgene (−) littermate controls. The GENE CHIP analysis indicated that over 200 genes were increased by at least 2.5 fold, and approximately 140 genes were downregulated by dox administration. Importantly, the gene most prominently induced after dox administration was YM (stimulation index of 64.1±0.5). AMCase was not present on the chip, but another chitinase family gene, BRP39, was the twelfth most prominently induced gene in the array (stimulation index of 7.1±0.5). It should be noted that dox administration did not cause significant alterations in gene expression of transgene (−) animals.

As AMCase was not present on the GENE CHIP, other methods, including RT-PCR, Northern blot analysis, and ribonuclease protection assays were employed. All indicated that AMCase is an important downstream target of IL-13. This further demonstrates that AMCase is induced during the course of and potentially involved in the pathogenesis of IL-13 induced respiratory inflammation.

Effects of Allosamidin in Murine Asthma Models: Allosamidin is a known potent and selective inhibitor of chitinases. Wild type mice were sensitized to OVA and challenged with OVA a number of days later. One day prior to OVA challenge, mice were randomized into two groups and received daily i.p. doses of allosamidin or of vehicle control. Similar to the symptoms of human asthma, the OVA sensitization and challenge model results in a brisk eosinophil- and lymphocyte-rich inflammatory response with prominent mucus metaplasia and goblet cell hyperplasia. Allosamidin administration resulted in a dose-dependent inhibition of total cell, eosinophil and lymphocyte influx in the OVA challenged lung (FIG. 16). The inhibitory effect was most prominent in the highest dose tested (10 mg/kg), and was still prominent at the lowest (1 mg/kg). Therefore, allosamidin inhibited antigen-induced inflammation in an art-recognized murine model of human asthma.

Similarly, six-week old transgene (+) IL-13 mice were randomized to receive fourteen daily doses i.p. of allosamidin (1 mg/kg) or vehicle control. The animals were then sacrificed and the IL-13 phenotype was evaluated. In comparison to transgene (+) mice that received the vehicle control, transgene (+) mice that received allosamidin injections displayed markedly decreased BAL fluid cell recovery, decreased tissue inflammation, and impressive decreases in BAL and tissue eosinophils and lymphocytes. Morphometric, histologic, and lung volume assessment analysis indicated that the allosamidin treated animals had decreased lung volumes and smaller alveoli than the littermate controls, indicating that allosamidin is a potent inhibitor of both IL-13 induced inflammation and lung remodeling. It is important to note that in these experiments, allosamidin administration commenced six weeks after the birth of the transgenic mice constitutively expressing IL-13, that is, after the asthma-like phenotype had commenced. Thus allosamidin treatment in these mice and COPD decreased the progression of lung pathology even after the pathologic response had been initiated. This is analogous to therapeutic situations in humans where pharmaceutical compositions are administered after respiratory inflammatory diseases have already been diagnosed and have progressed to some degree. These results indicate that inhibitors of a chitinase-like molecule can successfully treat diseases even after chronic pathology has been established.

Effects of Anti-AMCase Antibodies in Murine Asthma Models

Figure 18A:
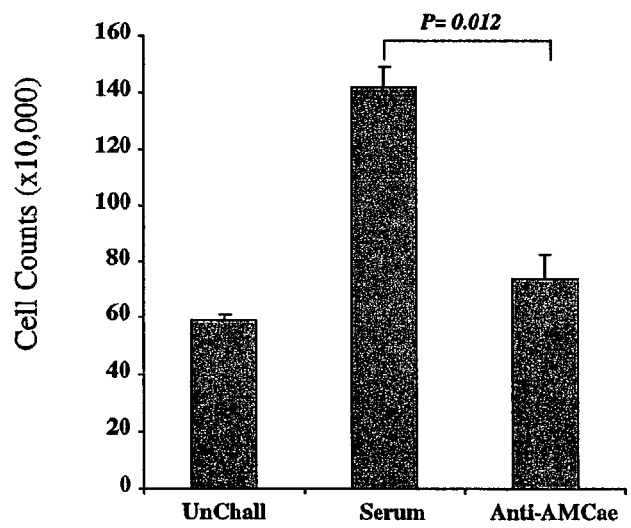
FIGS. 18A and 18B, depicts the effects of anti-AMCase antibodies on ovalbumin-induced BAL cell counts.
Figure 18B:
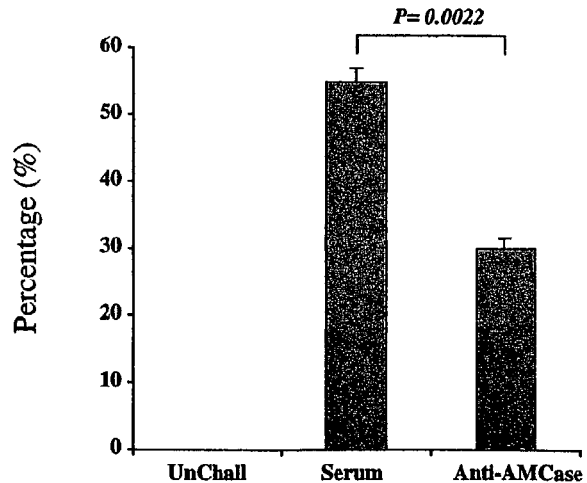

Wild type mice were sensitized to OVA and challenged with OVA a number of days later. One day prior to OVA challenge, mice were randomized into two groups and received daily doses of anti-AMCase antibodies or a serum control. Similar to the symptoms of human asthma, the OVA sensitization and challenge model results in a brisk eosinophil- and lymphocyte-rich inflammatory response with prominent mucus metaplasia and goblet cell hyperplasia. Anti-AMCase antibody administration resulted in a significant inhibition of total cell and eosinophil influx into the BAL fluid of these OVA challenged lungs (FIG. 18). A similar decrease in total and eosinophilic inflammation was noted in OVA sensitized and challenged long tissues. Therefore, anti-AMCase inhibited antigen-induced inflammation in an art-recognized murine model of human asthma.

AMCase Expression in Human Lung Tissue

The observations in the art-recognized mouse model of human asthma were extended to assessing the expression of AMCase in human lung tissue that was obtained at autopsy using in situ hybridization. Briefly, similarly to the protocols described previously elsewhere herein relating to in situ hybridization for detection of mouse AMCase and Ym-1 mRNA, normal and asthmatic lung tissues were obtained through biopsies and fixed in formaldehyde and processed into paraffin. Five micron sections were cut, deparaffinized, and treated with proteinase K (20 µg/ml, 37° C., 20 min). Tissues were then treated with 0.1 M triethylnolamine/0.25% acetic anhydride (pH 8) for 10 min at room temperature and rinsed in PBS.

The templates for ISH probes for human AMCase were purchased from Research Genetics, Inc (Huntsville, Ala.) as expressed sequence tag (EST) clones 5182357. The clone was generated using vector pCMV-SPORT6 comprising T7 and SP6 promoter sequences flanking the insert fragment. The sequence of the clone matched human AMCase mRNA from nucleotide 769–1538 (SEQ ID NO:14). The sequence of the clone was confirmed by nucleotide sequencing at Keck Biotechnology Laboratory at Yale University. Sense and antisense RNA probes were in vitro transcribed and labeled with a digoxigenin RNA labeling kit (Roche, Indianapolis, Ind.), denatured at 65° C., and added to commercially available hybridization buffer (Ambion, Austin, Tex.) at 6 ng/µl, and the hybridization mixture was incubated with tissue overnight at 52° C. The tissues were then washed twice with 4×SSC for 5 minutes at room temperature, twice with 2×SSC for 10 minutes at 37° C., and incubated with RNase A (10 µg/ml) for 45 minutes at 37° C. This was followed by two 10-minute washes in 2×SSC at room temperature and three 20-minute washes in 0.2×SSC at 50° C. Probes were detected by overnight incubation with sheep antibodies to digoxigenin conjugated with alkaline phosphatase (Roche) followed by 4-nitroblue tetrazolium chloride/5-bromo-4-chloro-3-indoylphosphate, as described by the manufacturer.

Figure 19C:
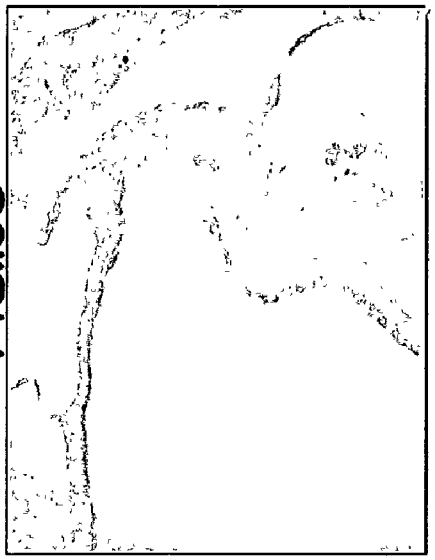
FIGS. 19A through 19D are images depicting detectable AMCase mRNA using in situ hybridization in autopsy lung samples from a patient with asthma using an AMCase antisense probe (FIG. 19A). AMCase mRNA was not detected in histologically normal control lung tissue obtained at autopsy from patients without lung disease using the antisense probe (FIG. 19B). In situ hybridization using a sense probe did not detect AMCase in either fatal asthma tissue (FIG. 19C) or control tissue (FIG. 19D). Epithelial cell (thick arrow) and macrophage (thin arrow) staining in fatal asthma was detected (FIG. 19A).
Figure 19D:
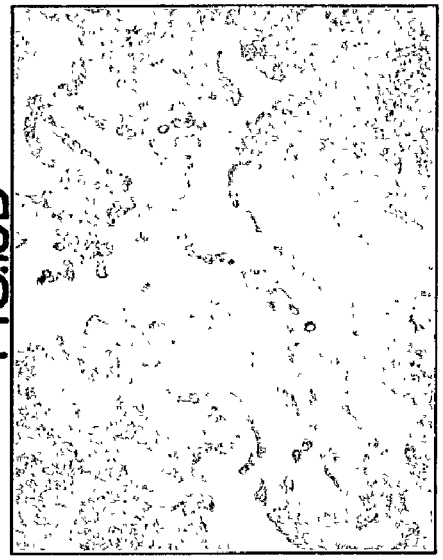
Figure 19A:
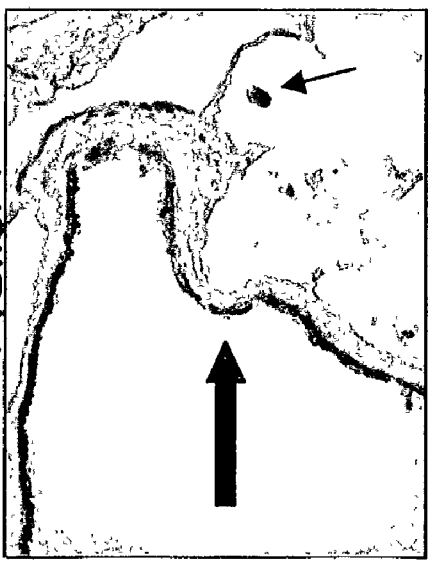
Figure 19B:
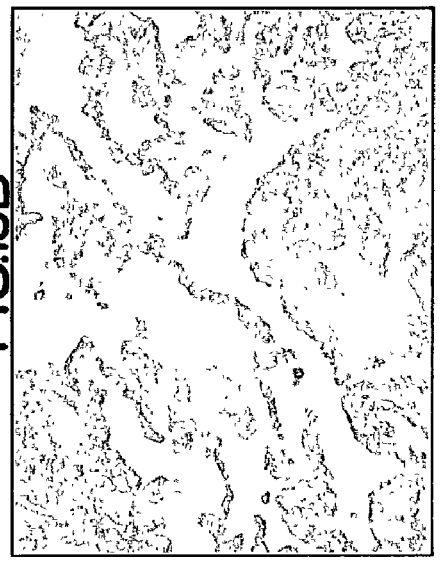

Expression of AMCase in histologically normal human lung tissue ("control tissue") was compared with AMCase expression in tissues obtained from human patients that had succumbed due to fatal asthma ("fatal asthma"). Using in situ hybridization, AMCase mRNA was detected in fatal asthma lung samples but not in control lung tissue using a sense probe (FIGS. 19A and 19B, respectively). AMCase mRNA was localized to epithelial cells and macrophages in fatal asthma tissue. Further, a sense probe did not detect mRNA encoding AMCase in either fatal asthma or control lung tissue, demonstrating the specificity of the probe. In addition, a poly-dT probe highlighted intact mRNA in both samples.

Figure 19E:
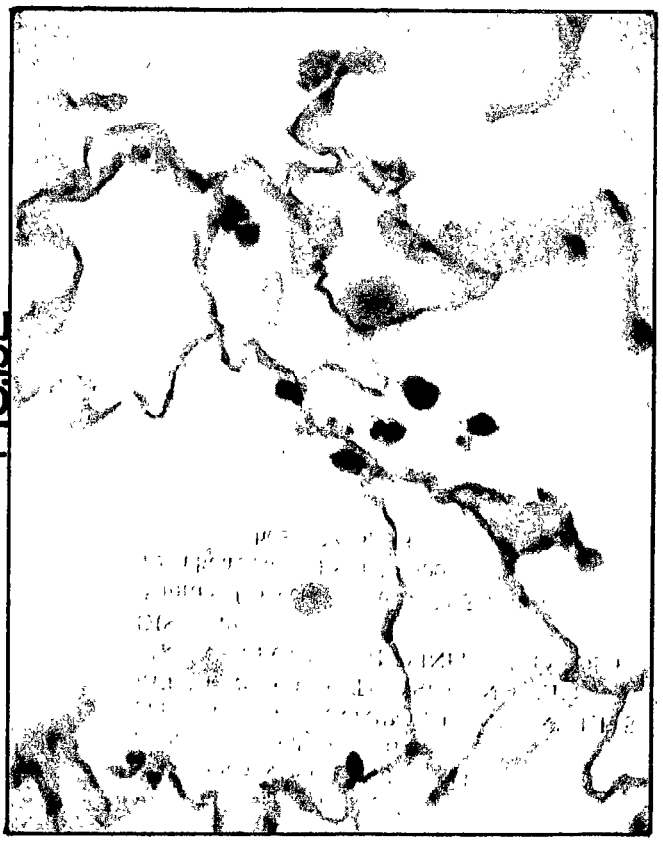
FIGS. 19E and 19F are images depicting detectable AMCase mRNA using in situ hybridization in alveolar macrophages present in autopsy lung samples from patients with asthma using an AMCase antisense probe (FIG. 19E). AMCase mRNA was not detected using a sense probe (FIG. 19F). Further, AMCase mRNA was not detected in control lung tissue obtained from patients without lung disease using the antisense or sense probes.
Figure 19F:
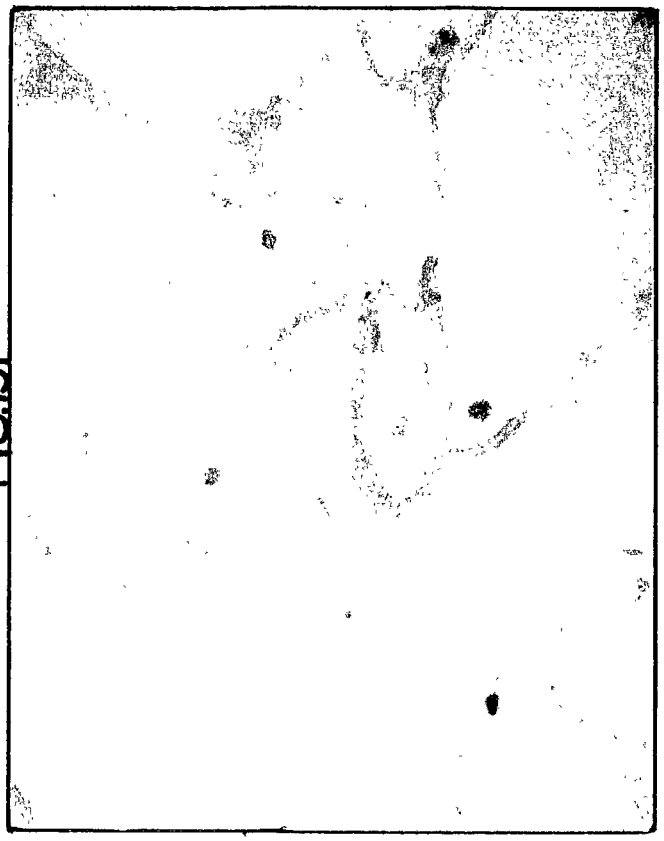

Expression of AMCase mRNA in human alveolar macrophages was also assessed. In situ hybridization using an AMCase antisense probe demonstrated detectable AMCase mRNA in alveolar macrophages in fatal asthma lung samples (FIG. 19E) but not in the control samples. AMCase mRNA was not detected in fatal asthma lung samples using a sense AMCase probe, demonstrating the specificity of the in situ hybridization procedure.

These data confirm that the results obtained using the art-recognized mouse model of human asthma are in accordance with human in vivo data. That is, the data disclosed herein demonstrate, for the first time, that AMCase mRNA expression is greatly increased, and correlated with, asthma in humans, since AMCase mRNA is present in detectable levels in fatal asthma lung tissue, but is not detectable in histologically normal lung tissue. These results further support the demonstration that expression of chitinase-like molecules is associated with and/or mediates inflammatory disease in mammals. Thus, the data disclosed herein further support that inhibition of AMCase, using a chitinase-like molecule inhibitor, can treat and/or prevent an inflammatory disease, such as, but not limited to, asthma, in a mammal, including, a human patient.

Discussion

The present invention is based, in part, on experimental evidence strongly suggesting that the Th2 inflammatory responses characteristic of allergies, atopic asthma and the inflammatory and airway remodeling responses associated with these disorders have evolved from the Th2 inflammatory responses first developed to combat parasites and other pathogens. Asthma and other inflammatory diseases are thus the consequence of poorly controlled Th2 responses elicited in a parasite and pathogen-independent manner.

A vast array of parasites and other pathogens contain chitin. It is an essential component in the exoskeletons of crustaceans and insects, the walls of fungi, the digestive tracts of insects, the microfilarial sheath of parasitic nematodes and components of helminthic parasites. Chitin is a polymer of N-acetylglucosamine residues in a β-1,4 linkage and is the second most abundant polysaccharide in nature, behind cellulose, and has no mammalian counterpart. Chitin often comprises the exterior of parasites and other pathogens because, depending on its thickness, it can be a rigid or flexible coating vital to protecting the organisms from the host defenses and from the surrounding environment. Thusly, because it is present at the host/pathogen interface, chitin is a prominent antigen since it is exposed to the immune system. In fact, chitin has demonstrated to be a potent T and B cell adjuvant which augments immunoglobulin responses to poorly immunogenic peptides, and which can shift immune responses in a Th1 direction (Seferian and Martinez, 2000, Vaccine 19:661–668; Shibata et al., 2000 J. Immunol. 164:1314–1321).

Given the enormous body of evidence demonstrating the co-evolution of parasites and humans, especially in regards to host immune responses, and the complete lack of chitin in mammals, it is reasonable to believe, without intending to be bound by any particular theory, that mammals developed chitinases as an innate defense against chitin-bearing parasites. Chitinases have been identified in mammals. Chitotriosidase and YKL-39 have been described in humans, YM protein has been described in the mouse, and acidic mammalian chitinase (AMCase), oviductin, and YKL-40 have been described in both mice and humans (Boot et al., 2001, J. Biol. Chem. 276:6770–6778; Boot et al., 1998, J. Biol. Chem. 273:25680–25685; Ward et al., 2001, Am. J. Pathol. 158:323–332; Chang et al., 2001, J. Biol. Chem. 276: 17497–17506; Jin et al., 1998, Genetics 54:316–322; Bleau et al., 1999, EXS 87:211–221). Despite conflicting reports and some sequence homology to microbial chitinases, only chitotriosidase and AMCase have demonstrated true chitinase activity (Boot et al., 2001, J. Biol. Chem. 276:6770–6778). Of the mammalian chitinases, both YM-1 and AMCase have been identified as having chemotactic and growth factor-like properties. YM-1 is a single chain peptide of 45 kDa that readily forms crystals under physiological conditions. YM family proteins have been identified as both eosinophilic and a $CD4^+$ T-cell attractant, as well as having lectin activity (Owhashi et al., 2000, J. Biol. Chem. 275:12791286; Chang et al., 2001, J. Biol. Chem. 276: 17497–17506). AMCase is a 50 kDa protein that demonstrates chitinase activity. It has also been reported as a fibroblast growth promoting agent (Guoping et al., 1997, J. Cell. Biochem. 67:257–264). As demonstrated by the data disclosed herein, both YM family proteins and AMCase are highly expressed in the lung of IL-13 induced, and Th2 mediated asthma models.

Without wishing to be bound by any particular theory, when viewed in combination with the role of chitin in the asthmatic condition, the novel discovery of the role of chitinases in asthma and other respiratory inflammatory diseases may be viewed as follows. In a non-atopic, non-asthmatic subject, exposure to chitin as an antigen, possibly after exposure to a parasite or fungus, polarizes the immune response towards a Th1 pathway, which may or may not effectively combat the parasite. However, in the atopic subject or one genetically disposed to asthma or atopy, IL-13 and/or IL-4 are produced which upregulate the expression of YM, AMCase, and possibly other chitinases and chitinase-like molecules. Chitin, as detailed earlier, augments IgE production. YM family proteins, alone or in combination with other molecules, possess eosinophil and $CD4^+$ T cell chemotactic properties. Therefore, YM proteins can attract eosinophils to the lung, as well as cause tissue damage mediated by its carbohydrate-binding and crystal-forming characteristics. AMCase eventually degrades the chitin to eliminate the pathogen. Because of the Th1 inducing properties of chitin, AMCase activity and subsequent chitin degradation steers the immune system towards a Th2 response characteristic of atopy and asthmatic inflammatory diseases.

The present invention includes methods and therapeutics for the treatment of asthma, COPD, and other inflammatory diseases using chitinase-like molecule inhibitors. The invention further comprises methods of identifying novel therapeutics for the treatment of asthma, COPD, and other inflammatory diseases relating to IL-13, IL-4 chitinases and chitinase-like molecule inhibitors.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating asthma in a human, said method comprising administering to said human an effective amount of an antibody that specifically binds to human acidic mammalian chitinase (AMCase), SEQ ID NO: 15, and does not inhibit the AMCase chitinase activity, thereby treating said asthma in said human.

2. The method of claim 1, wherein said antibody is a monoclonal antibody.

3. The method of claim 1, wherein said antibody is a humanized antibody.

4. The method of claim 1, wherein said antibody is a synthetic antibody.

5. The method of claim 1, wherein said antibody is selected from the group consisting of Fab, Fv, F(ab)$_2$, and an scFv.

* * * * *

UNITED STATES PATENT AND TRADEMARK OFFICE
CERTIFICATE OF CORRECTION

PATENT NO. : 7,214,373 B2  
APPLICATION NO. : 10/202436  
DATED : May 8, 2007  
INVENTOR(S) : Jack Elias et al.

Page 1 of 1

It is certified that error appears in the above-identified patent and that said Letters Patent is hereby corrected as shown below:

On column 1 of the specification, beginning at line 16 through line 20, please delete the paragraph and replace with the following paragraph:

-- This invention was made with government support under HL056389, HL064242 and HL066571 awarded by National Institutes of Health. The government has certain rights in the invention. --

Signed and Sealed this
Fourth Day of August, 2015

Michelle K. Lee
*Director of the United States Patent and Trademark Office*